Figure 1:
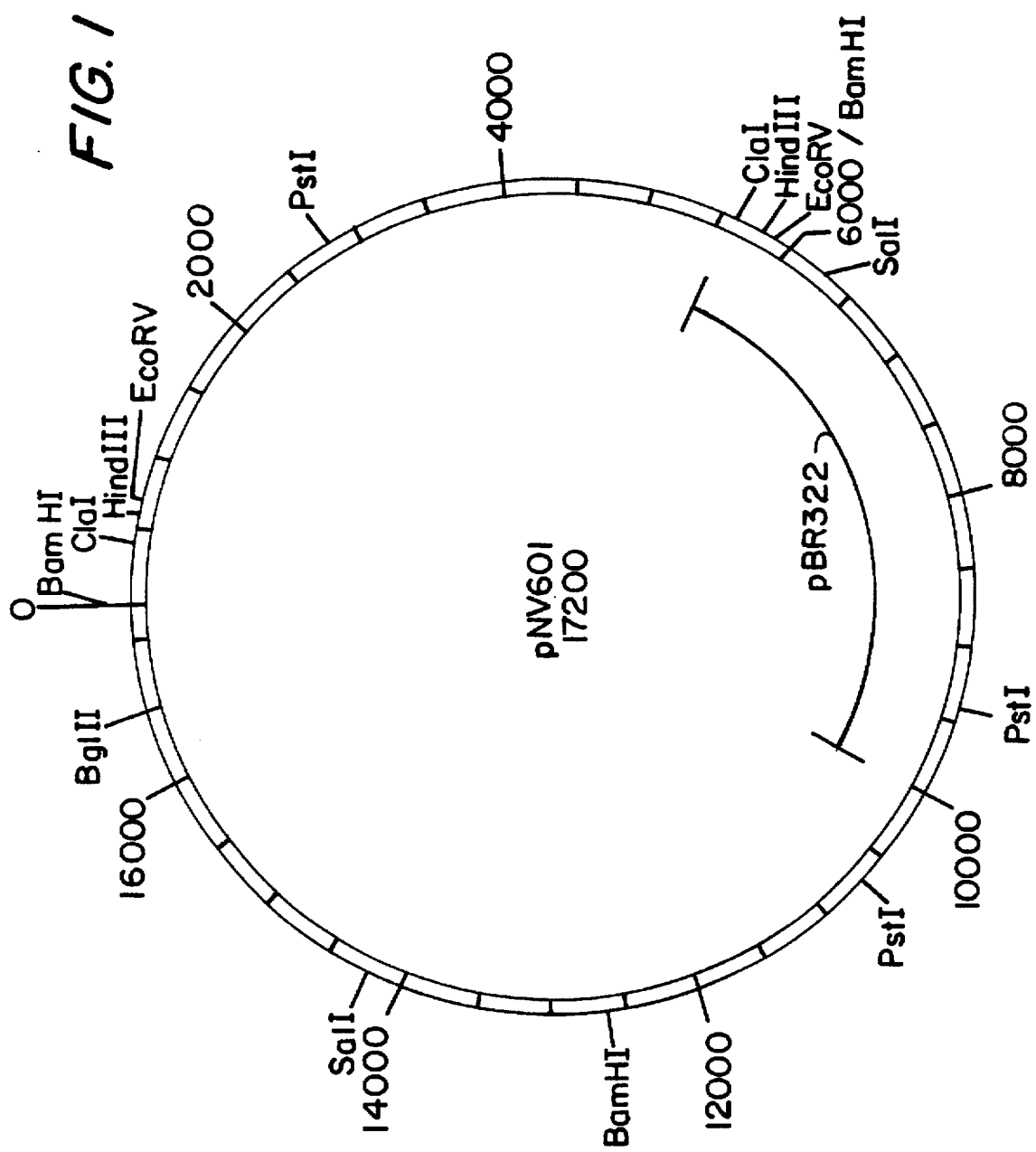

US005698415A

United States Patent [19]

Jørgensen et al.

[11] Patent Number: 5,698,415
[45] Date of Patent: Dec. 16, 1997

[54] BACILLUS PROMOTER DERIVED FROM A VARIANT OF A BACILLUS LICHENIFORMIS X-AMYLASE PROMOTER

[75] Inventors: Steen Troels Jørgensen, Allerød; Børge Krag Diderichsen, Birkerød, both of Denmark

[73] Assignee: Novo Nordisk A/s, Bagsvaerd, Denmark

[21] Appl. No.: 240,748

[22] PCT Filed: Nov. 13, 1992

[86] PCT No.: PCT/DK92/00338

§ 371 Date: May 10, 1994

§ 102(e) Date: May 10, 1994

[87] PCT Pub. No.: WO93/10249

PCT Pub. Date: May 27, 1993

[30] Foreign Application Priority Data

Nov. 13, 1991 [WO] WIPO .............. PCT/DK91/00343

[51] Int. Cl.$^6$ .............. C12P 21/06; C12N 1/21; C12N 15/75; C12N 15/11
[52] U.S. Cl. .................. 435/69.1; 435/252.31; 435/320.1; 536/24.1
[58] Field of Search .............. 435/69.5, 320.1, 435/252.31, 69.1; 935/55; 536/24.1

[56] References Cited

U.S. PATENT DOCUMENTS 4,769,327  9/1988  Stephens et al. .............. 435/69.8

OTHER PUBLICATIONS

Laoide et al., J. Bacteriol., vol. 171, pp. 2435–2442 (1989).
Sibakov et al., Eur. J. Biochem., vol. 145, pp. 567–572 (1984).
Yuuki et al., J. Biochem. vol. 98, No. 5, pp. 1147–1156 (1985).

*Primary Examiner*—Nancy T. Vogel
*Attorney, Agent, or Firm*—Steve T. Zelson, Esq.; Valeta Gregg, Esq.

[57] ABSTRACT

A Bacillus promoter included in DNA sequence (SEQ ID#1), wherein each of $N^1$-$N^9$ is A, T, C or G with the exception that $N^2$-$N^9$ do not together form the sequence ATGTTTCA or GTGTTTCA, or a functional homologue of said sequence.

32 Claims, 28 Drawing Sheets

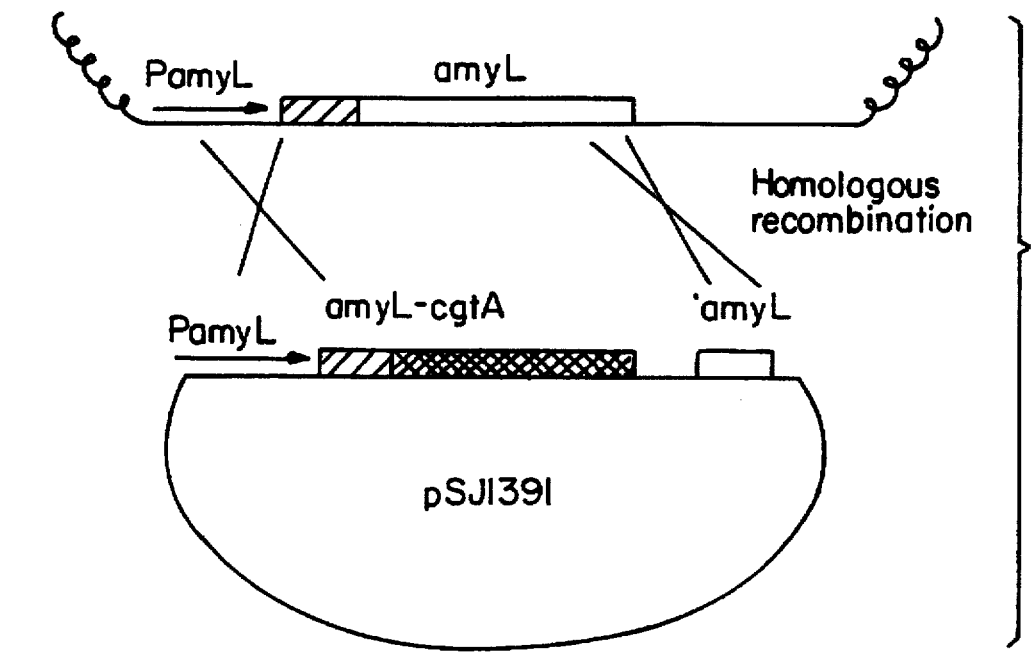
FIG. 26A
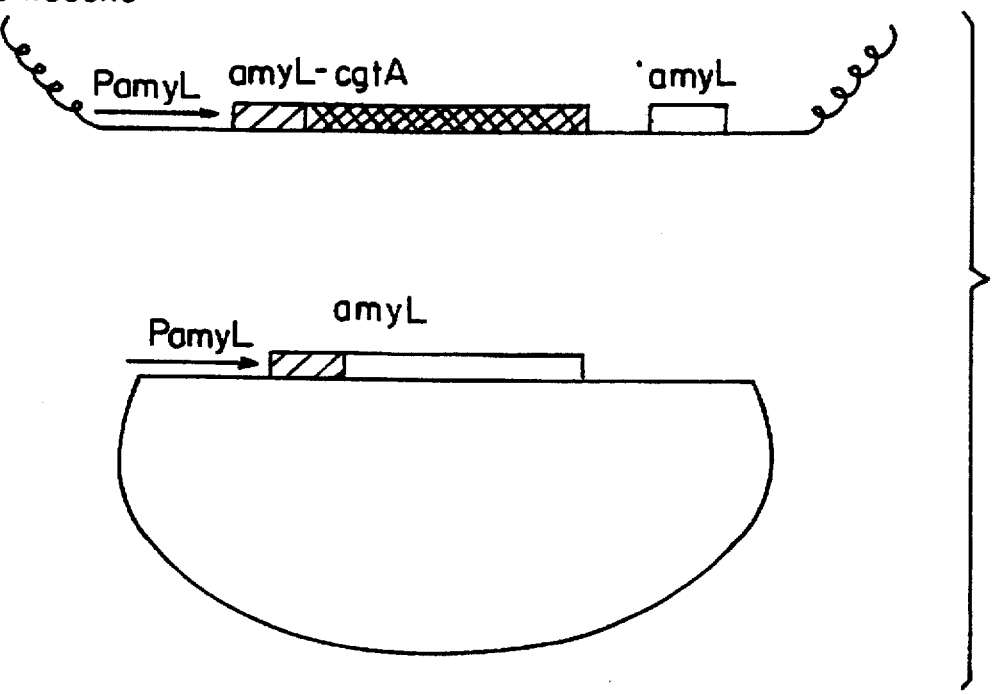
FIG. 26B

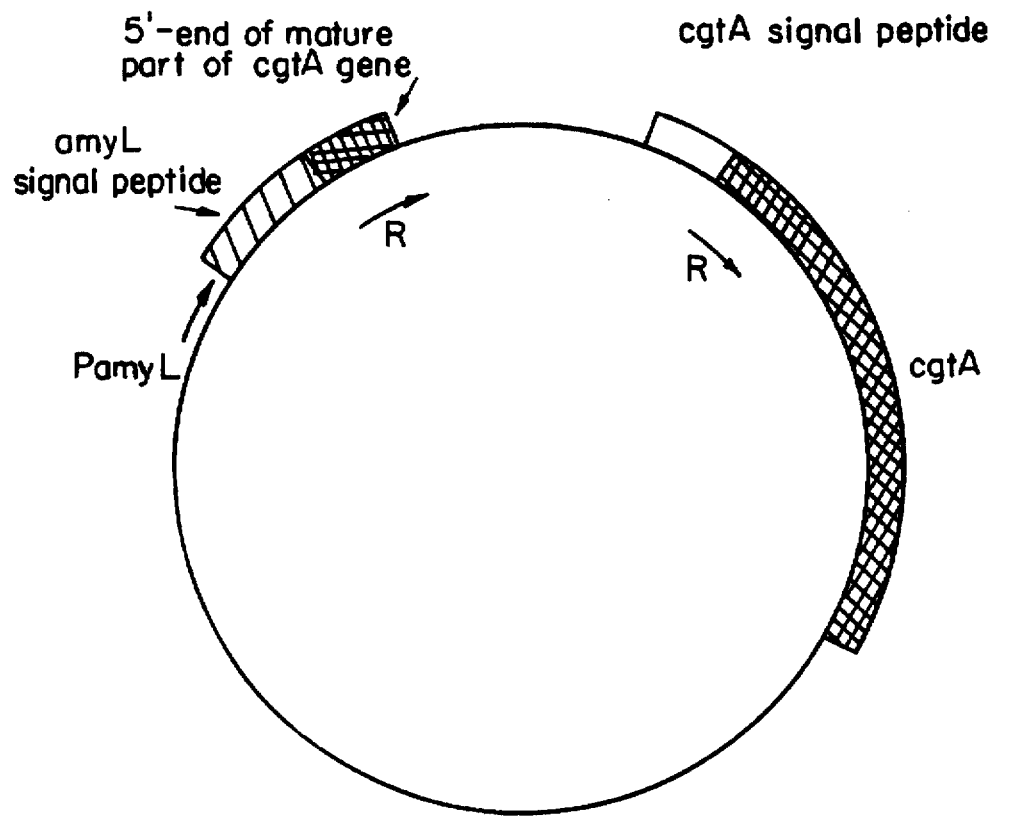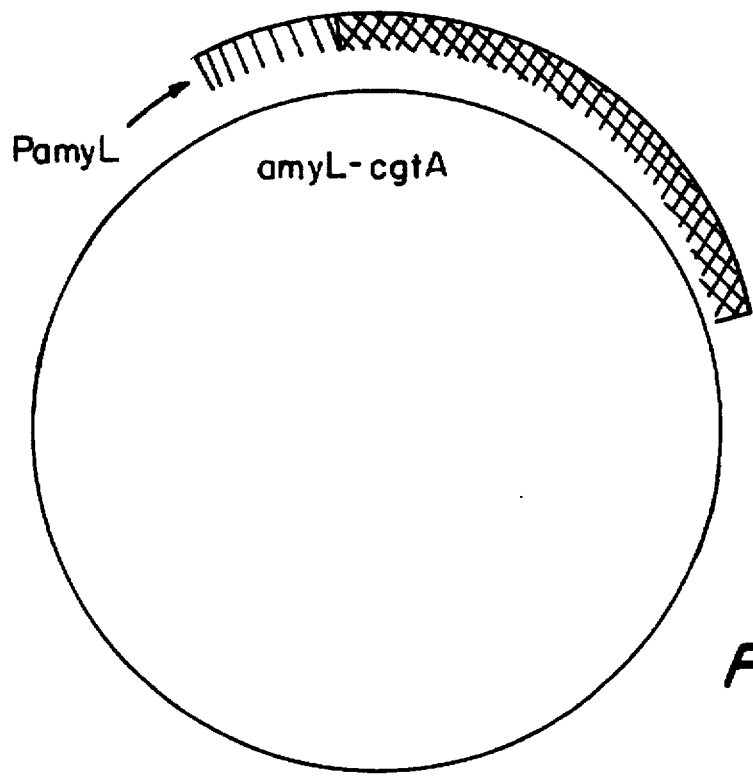
FIG. 27

BACILLUS PROMOTER DERIVED FROM A VARIANT OF A BACILLUS LICHENIFORMIS X-AMYLASE PROMOTER

CROSS-REFERENCE TO RELATED APPLICATIONS

This application is a 35 U.S.C. 371 national stage application of PCT/DK92/00338 filed Nov. 13, 1992, the contents of which are incorporated herein by reference.

FIELD OF THE INVENTION

The present invention relates to a *Bacillus licheniformis* promoter, a DNA construct comprising said promoter, A host cell transformed with said DNA construct and a method of producing a protein in Bacillus by means of the promoter.

BACKGROUND OF THE INVENTION

Various promoter sequences of the *Bacillus licheniformis* α-amylase gene have been described previously. Thus, M. Sibakov and L Palva, *Eur. J. Biochem.* 145, 1984, pp. 567–572, describe the isolation and determination of the 5' end of the *Bacillus licheniformis* α-amylase gene, including the promoter sequence; T. Yuuki et al., *J. Biochem.* 98, 1985, pp. 1147–1156, show the complete nucleotide sequence of the *Bacillus licheniformis* α-amylase gene, including the promoter sequence; and B. M. Laoide et al., *J. Bacteriol.* 171(5), 1989, pp. 2435–2442, discuss catabolite repression of the *Bacillus licheniformis* α-amylase gene from a region around the 5' end of the gene and show the sequence of this region.

SUMMARY OF THE INVENTION

The present inventors have surprisingly found that a novel promoter homologous to the previously published promoter sequences gives rise to a dramatically increased yield of a protein when the gene coding for the protein is transcribed from the promoter.

Accordingly, the present invention relates to a Bacillus promoter included in the following DNA sequence

```
GCATGCGTCC TTCTTTGTGC TTGGAAGCAG AGCCCAATAT TATCCCGAAA

CGATAAAACG GATGCTGAAG GAAGGAAACG AAGTCGGCAA CCATTCCTGG

GACCCATCCG TTATTGACAA GGCTGTCAAA CGAAAAAGCG TATCAGGAGA

TTAACGACAC GCAAGAAATG ATCGAAAAAA TCAGCGGACA CCTGCCTGTA

CACTTGCGTC CTCCATACGG CGGGATCAAT GATTCCGTCC GCTCGCTTTC

CAATCTGAAG GTTTCATTGT GGGATGTTGA TCCGGAAGAT TGGAAGTACA

AAAATAAGCA AAAGATTGTC AATCATGTCA TGAGCCATGC GGGAGACGGA

AAAATCGTCT TAATGCACGA TATTTATGCA ACGTTCGCAG ATGCTGCTGA

AGAGATTATT AAAAAGCTGA AAGCAAAAGG CTATCAATTG GTAACTGTAT

CTCAGCTTGA AGAAGTGAAG AAGCAGAGAG GCTATTGAAT AAATGAGTAG

AAAGCGCCAT ATCGGCGCTT TTCTTTTGGA AGAAAATATA GGGAAAATGG

TAN¹TTGTTAA AAATTCGGAA TATTTATACA ATATCATN²N³N⁴

N⁵N⁶N⁷N⁸N⁹CATTG AAAGGGGAGG AGAATC (SEQ ID NO: 1)
``` wherein each of $N^1$–$N^9$ is A, T, C or G with the exception that $N^2$–$N^9$ do not together form the sequence ATGTTTCA or GTGTTTCA, or a functional homologue of said sequence.

In the the previously published sequences, $N^1$ is either T (cf. T. Yuuki et al., supra) or C (B. M. Laoide et al., supra), while $N^2$–$N^9$ is either ATGTTTCA (T. Yuuki et al., supra, and B. M. Laoide et al., supra) or GTGTTTCA (cf. M. Sibakov, supra). Several papers discuss catabolite repression of Bacillus genes, including the *B. licheniformis* α-amylase gene. Thus, B. M. Laoide et al, supra, and B. M. Laoide and D. J. McConnell, *J. Bacteriol.* 171, 1989, pp. 2443–2450, map the cis sequences essential for mediation of catabolite repression of amyL in *B. subtilis* to a 108 bp region downstream from the promoter and upstream from the signal sequence cleavage site. They identify an inverted repeat sequence, TGTTTCAC-20 bp-ATGAAACA, in this region but note that deletion into the left-hand part of this sequence either abolished or altered expression without affecting catabolite repression. They identify sequences homologous to the left-hand part of the amyL inverted repeat (5'-A/T T G T N A/T-3') around the transcription initiation sites in a number of *B. subtilis* catabolite-repressible genes.

Y. Miwa and Y. Fujita, *Nucl. Acids Res.* 18, pp. 7049–7053, limit the cis sequences involved in catabolite repression of the *B. subtilis gnt* operon to a 11 bp region.

Within this 11 bp region is a 8 bp sequence, ATTGAAAG, which the authors claim could be a consensus sequence involved in catabolite repression in the genus Bacillus, as it was found in other catabolite repressible Bacillus genes. Interestingly, in the *B. licheniformis* α-amylase gene, the consensus sequence shown above immediately follows the left-hand part of the inverted repeat sequence identified by Laoide et al.

M. J. Weickert and G. H. Chambliss, *Proc. Natl. Acad. Sci. USA* 87, pp. 6238–6242, describe site-directed mutagenesis of a catabolite repression operator sequence in *B. subtilis* from the amyE gene. They observe that hyperproduction and catabolite repression of amylase were both affected by mutations in the same region, and sometimes by the same mutation. They found that the *B. subtilis* α-amylase catabolite repression operator shares significant homology with sequences in other Bacillus amylase gene regulatory regions and with other catabolite repressed genes. The consensus sequence they identified is located from position +70 to +64 with respect to the *B. licheniformis* α-amylase transcription initiation site.

At least one group considers the sequence $N^2-N^9$ (according to the present nomenclature) to form an essential part of the cis sequence required for catabolite repression, while another group points to an immediately adjacent sequence. It is noteworthy that $N^2-N^9$ form part of an inverted repeat sequence. Modifications of these sequences might well influence the transcription levels obtained from the amyL promoter. It cannot, however, be discounted, that substitutions in other parts of the promoter sequence such as at $N^1$, may also influence the transcription levels obtained from the promoter.

In the present context, the term "functional homologue" is intended to indicate a promoter sequence with at least 70% sequence identity to the sequence shown above, which sequence, under comparable conditions, promotes a more efficient transcription of the gene it precedes than the promoter disclosed by T. Yuuki et al., supra, or B. Laoide et al., supra. The transcription efficiency may, for instance, be determined by a direct measurement of the amount of mRNA transcription from the promoter, e.g. by Northern blotting or primer extension, or indirectly by measuring the amount of gene product expressed from the promoter. The term is intended to include derivatives of the promoter sequence shown above, such as insertion of one or more nucleotides into the sequence, addition of one or more nucleotides at either end of the sequence and deletion of one or more nucleotides at either end of or within the sequence, provided that such modifications do not impair the promoter function of the sequence. Fragments of the sequence shown above are included in this definition of a functional homologue.

DETAILED DISCLOSURE OF THE INVENTION

The promoter of the invention may be derived from the genome of a suitable *Bacillus licheniformis* strain by hybridisation using oligonucleotide probes based on the promoter sequence known from T. Yuuki et al., supra, or B. Laoide et al., supra, in accordance with standard techniques (cf. Sambrook et al., *Molecular Cloning: A Laboratory Manual*, Cold Spring Harbor, N.Y., 1989). The known promoter sequence may be modified at one or more sites by site-directed mutagenesis in accordance with well-known procedures. The promoter sequence may also be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO J.* 3, 1984, pp. 801–805.

Examples of preferred promoters of the invention are those wherein $N^1$ is C or T; or wherein $N^7$ is A, G or C; in particular wherein $N^1$ is C and $N^7$ is A. Thus, $N^2-N^9$ together preferably form the sequence ATGTTACA, while $N^1$ is preferably C.

An example of a suitable fragment of the promoter sequence shown above has the following DNA sequence

CTATCAATTG GTAACTGTAT CTCAGCTTGA AGAAGTGAAG AAGCAGAGAG

GCTATTGAAT AAATGAGTAG AAAGCGCCAT ATCGGCGCTT TTCTTTTGGA

AGAAAATATA GGGAAAATGG TAN¹TTGTTAA AAATTCGGAA TATTTATACA

ATATCATN²N³N⁴ N⁵N⁶N⁷N⁸N⁹CATTG AAAGGGGAGG AGAATC (SEQ ID NO: 2)

wherein $N^1-N^9$ has the meaning indicated above.

In a preferred embodiment, the promoter of the invention is derived from a *B. licheniformis* gene, and in particular it is a variant of a *Bacillus licheniformis* α-amylase promoter.

In another aspect, the present invention relates to a DNA construct comprising a DNA sequence coding for a protein of interest preceded by a promoter sequence as described above. The protein of interest may advantageously be an enzyme, e.g. α-amylase, cyclodextrin glycosyl transferase or a protease. The DNA construct may advantageously also comprise a sequence coding for a signal peptide to ensure secretion into the culture medium of the protein in question on cultivating a cell transformed with the DNA construct.

According to the invention, the DNA construct may be present on an autonomously replicated expression vector. The vector further comprises a DNA sequence enabling the vector to replicate in the host cell. Examples of such sequences are the origins of replication of plasmids pUC19 (C. Yanisch-Perron et al., *Gene* 33, 1985, pp. 103–119), pACYC177 (A. C. Y. Chang and S. N. Cohen, *J. Bacteriol.* 134, 1978, pp. 1141–1156), pUB110 (Gryczan et al. 1978) or pIJ702 (E. Katz et al., *J. Gen. Microbiol.* 129, 1983, pp. 2703–2714). The vector may also comprise a selectable marker, e.g. a gene whose product confers antibiotic resistance such as ampcillin, chloramphenicol or tetracyclin resistance, or the dal genes from *B. subtilis* or *B. licheniformis* (B. Diderichsen, 1986). The procedures used to ligate the DNA sequence coding for the protein of interest, promoter and origin of replication are well known to persons skilled in the art (cf., for instance, Sambrook et al., *Molecular Cloning: A Laboratory Manual*, Cold Spring Harbor, N.Y., 1989).

Alternatively, the DNA construct may be present on the chromosome of the host cell. This is often an advantage as the DNA construct is more likely to be stably maintained in the host cell. Integration of the DNA construct into the host chromosome may be performed according to conventional methods, e.g. by homologous recombination. It should be noted that the promoter sequence, the DNA sequence encoding the protein of interest and optionally the signal sequence may be introduced into the host cell separately.

The host cell may suitably be a strain of Bacillus, in particular a strain of Bacillus licheniformis, Bacillus lentus, Bacillus brevis, Bacillus stearothermophilus, Bacillus alkalophilus, Bacillus amyloliquefaciens, Bacillus coagulans, Bacillus thuringiensis or Bacillus subtilis.

In a further aspect, the present invention relates to a process for producing a protein in Bacilli comprising culturing a Bacillus host cell transformed with a DNA construct or vector according to the invention under conditions permitting production of said protein, and recovering the resulting protein from the culture.

The medium used to cultivate the cells may be any conventional medium suitable for growing bacteria. The product of the expressed gene is preferably recovered from the culture. Recovery of the product may be done by conventional procedures including separating the cells from the medium by centrifugation or filtration, precipitating the proteinaceous components of the supernatant or filtrate by means of a salt, e.g. ammonium sulphate, followed, if necessary, by a variety of chromatographic procedures, e.g. ion exchange chromatography, affinity chromatography, or the like.

The invention is further described in the following example with reference to the appended drawings, in which the following abbreviations are used:

"pBR322" indicates pBR322-derived DNA;
"+ori pUB110" indicates the plus origin of replication of pUB110;
"rep" indicates the rep gene of pUB110;
"cat" indicates the chloramphenicol resistance gene of pC194;
"cgtA" indicates the Thermoanaerobacter CGTase gene;
"PamyM" indicates the promoter of the B. sterothermophilus maltogenic amylase gene (Diderichsen and Christiansen, 1988);
"bla" indicates the ampicillin resistance gene of pBR322;
"pKK233-2" indicates pKK233-2 derived DNA;
"PamyL" indicates the promoter of the B. licheniformis α-amylase gene;
"PamyQ" indicates the promoter of the B. amyloliquefaciens α-amylase gene;
"amyL-cgtA" indicates the fusion gene comprising the signal peptide coding part of the B. licheniformis α-amylase gene and the part of the Thermoanaerobacter CGTase gene coding for the mature enzyme;
"erm" indicates the erythromycin resistance gene of pE194;
"ori pE194" indicates the plus origin of replication and rep gene containing region of pE194; and
"'amyL" indicates a DNA fragment spanning the 3'-end of the B. licheniformis α-amylase gene.

Figure 2:
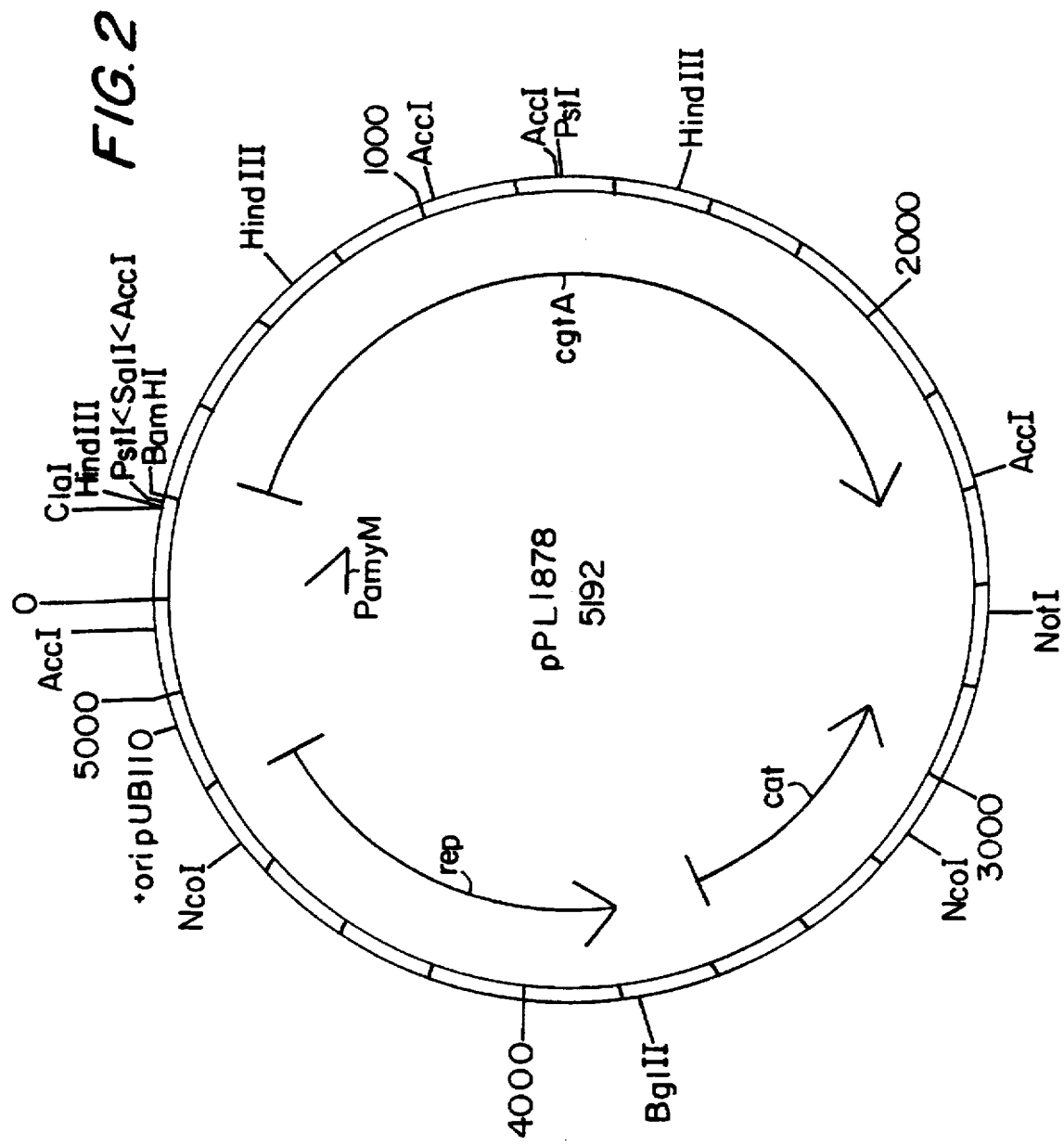
Figure 3:
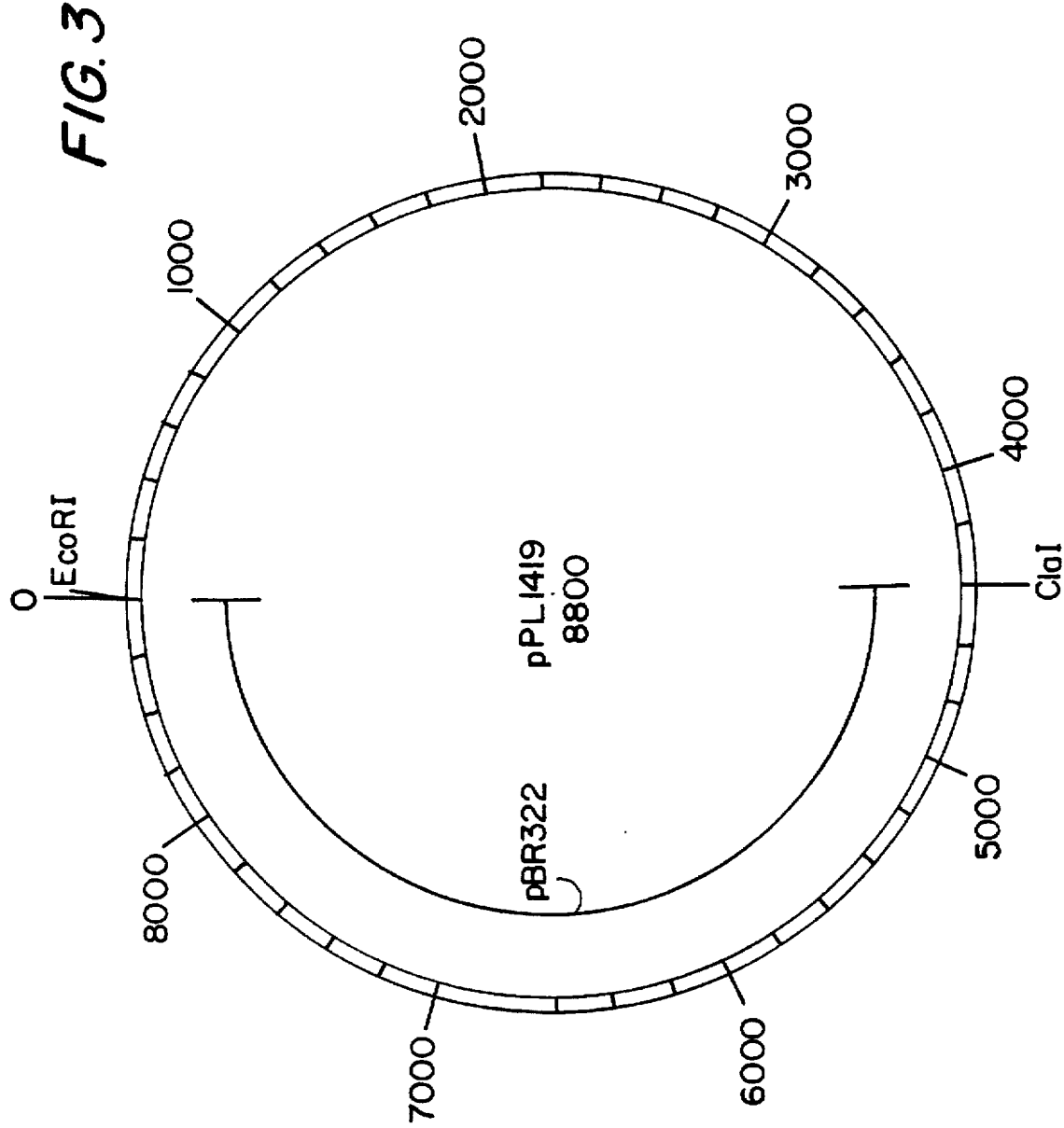
Figure 4:
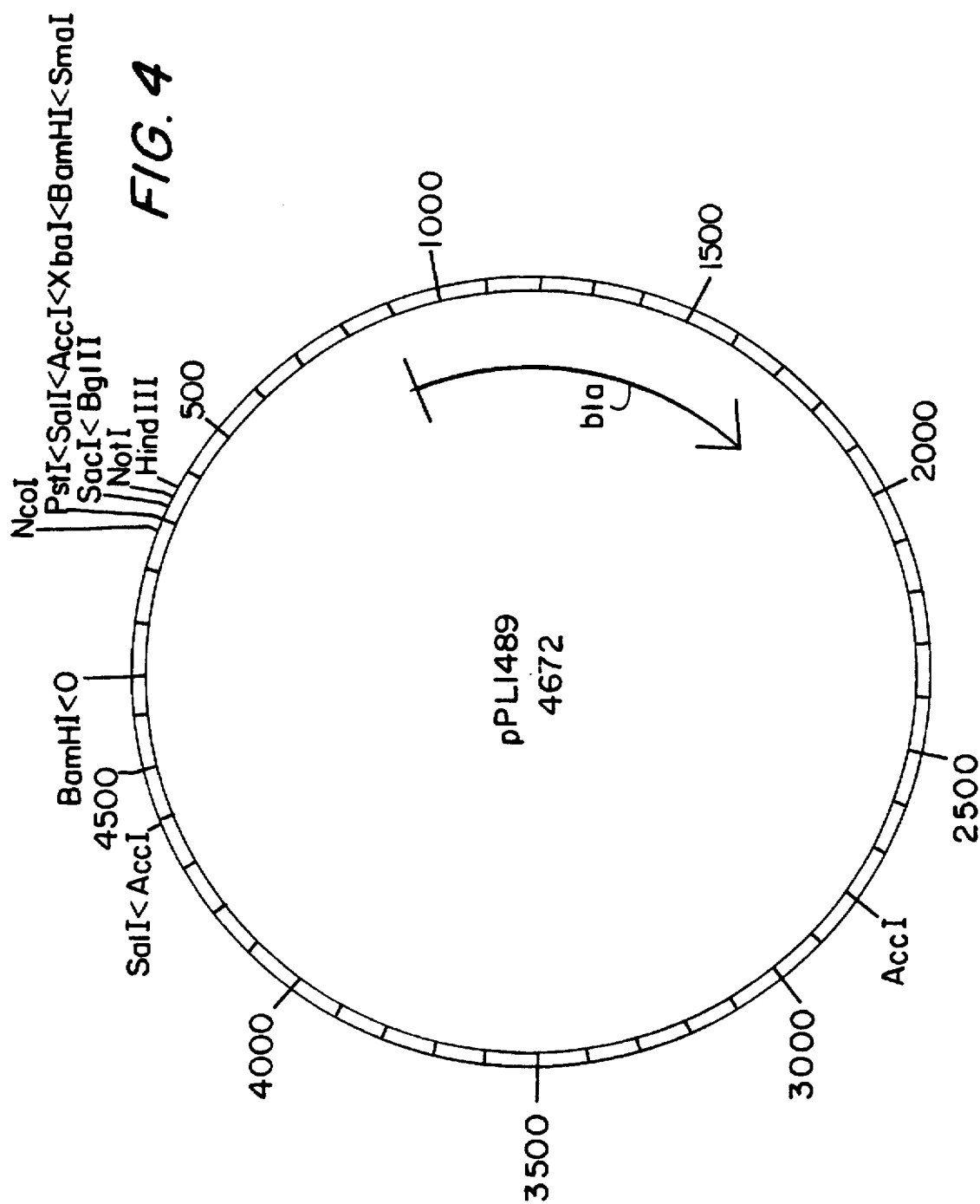
Figure 5:
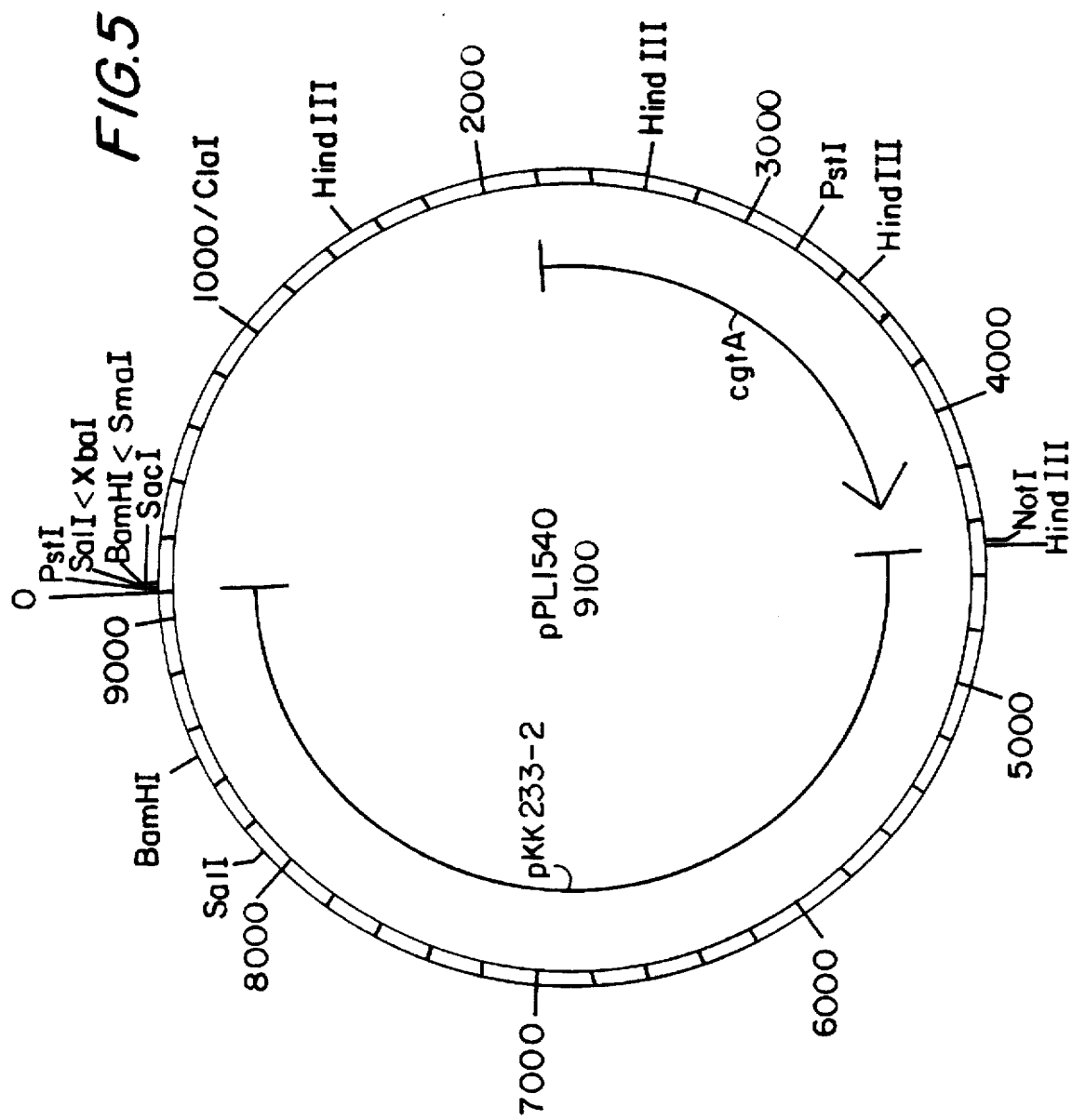
Figure 6:
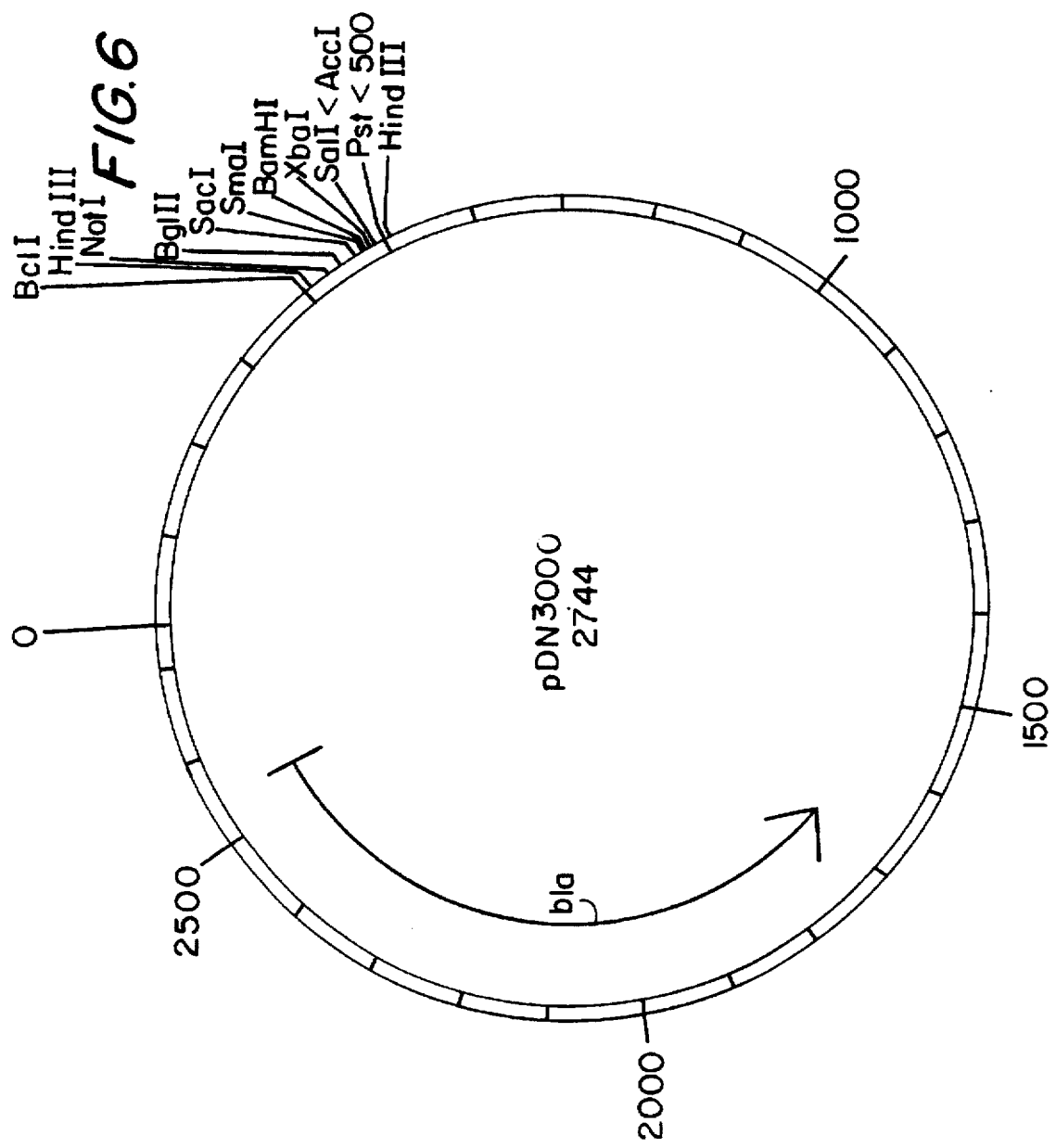
Figure 7:
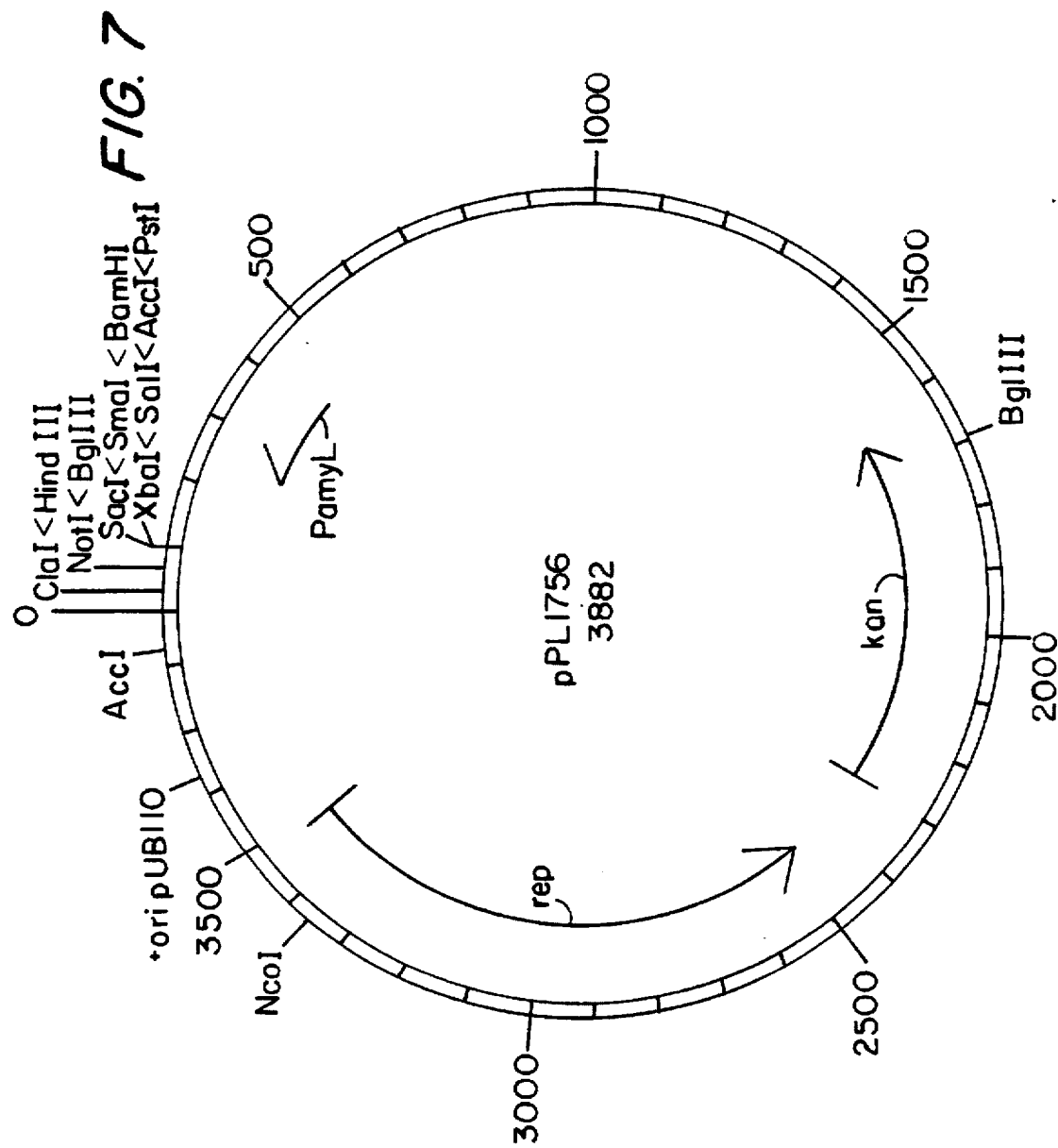
Figure 8:
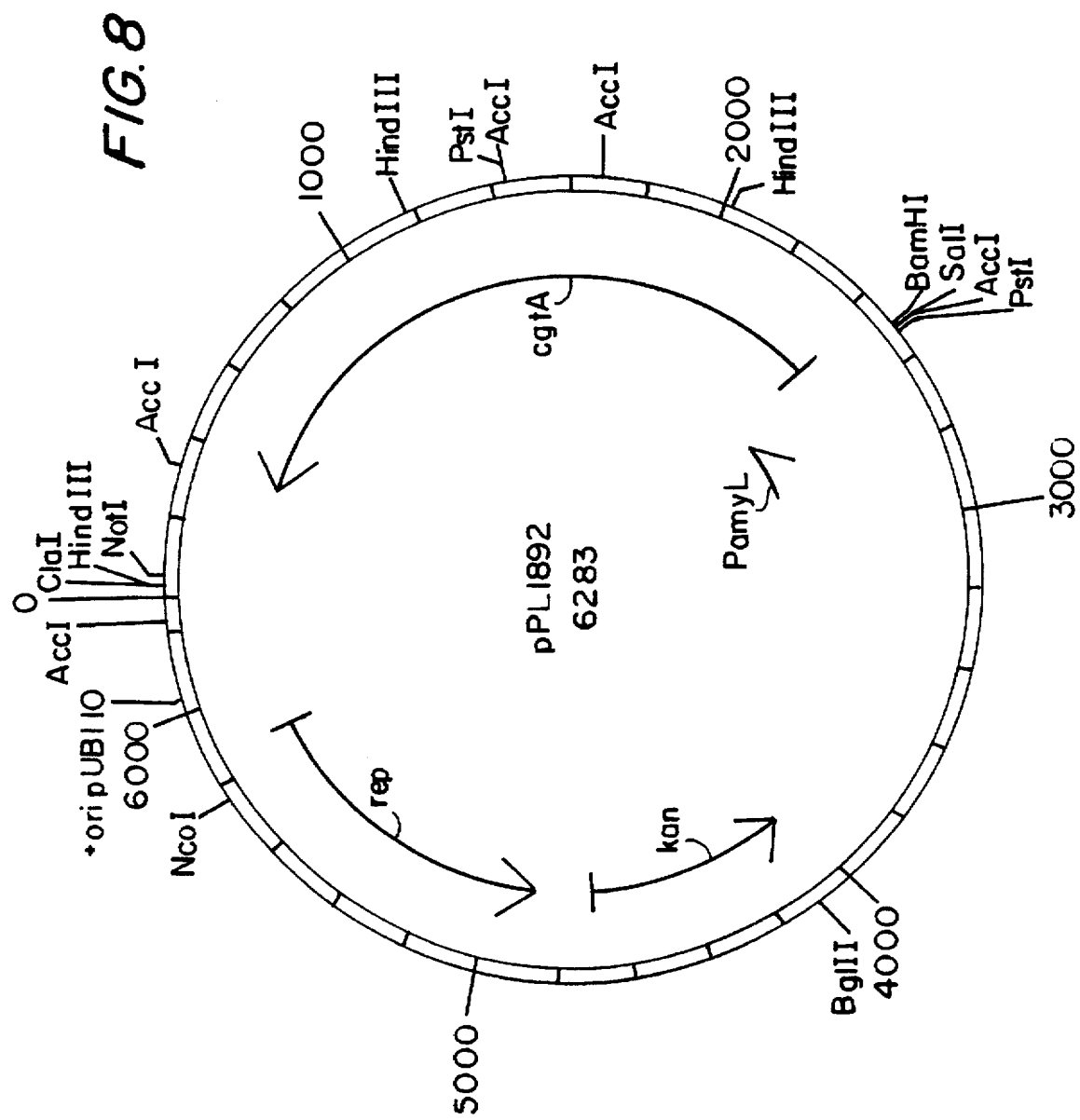
Figure 9:
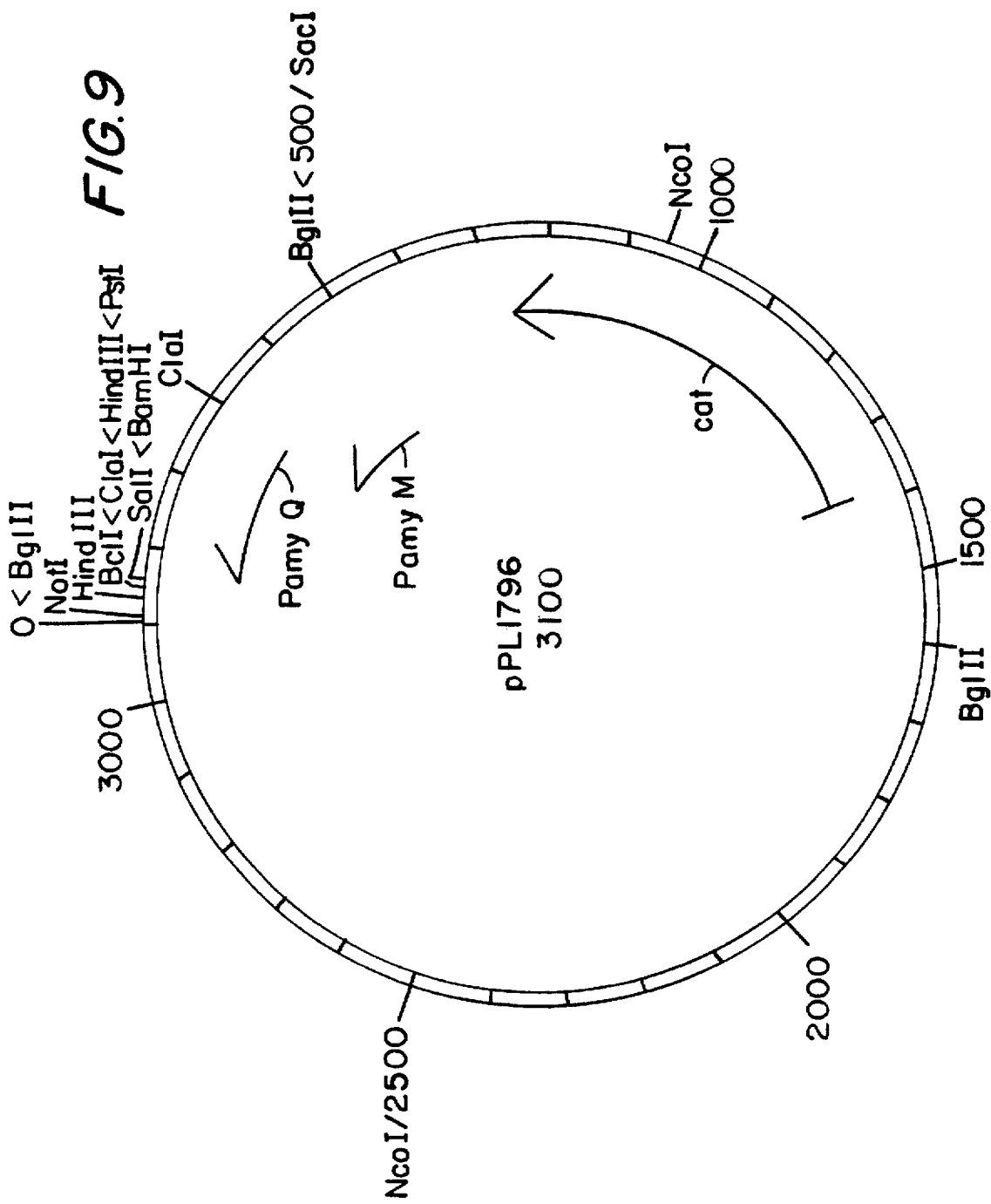
Figure 10:
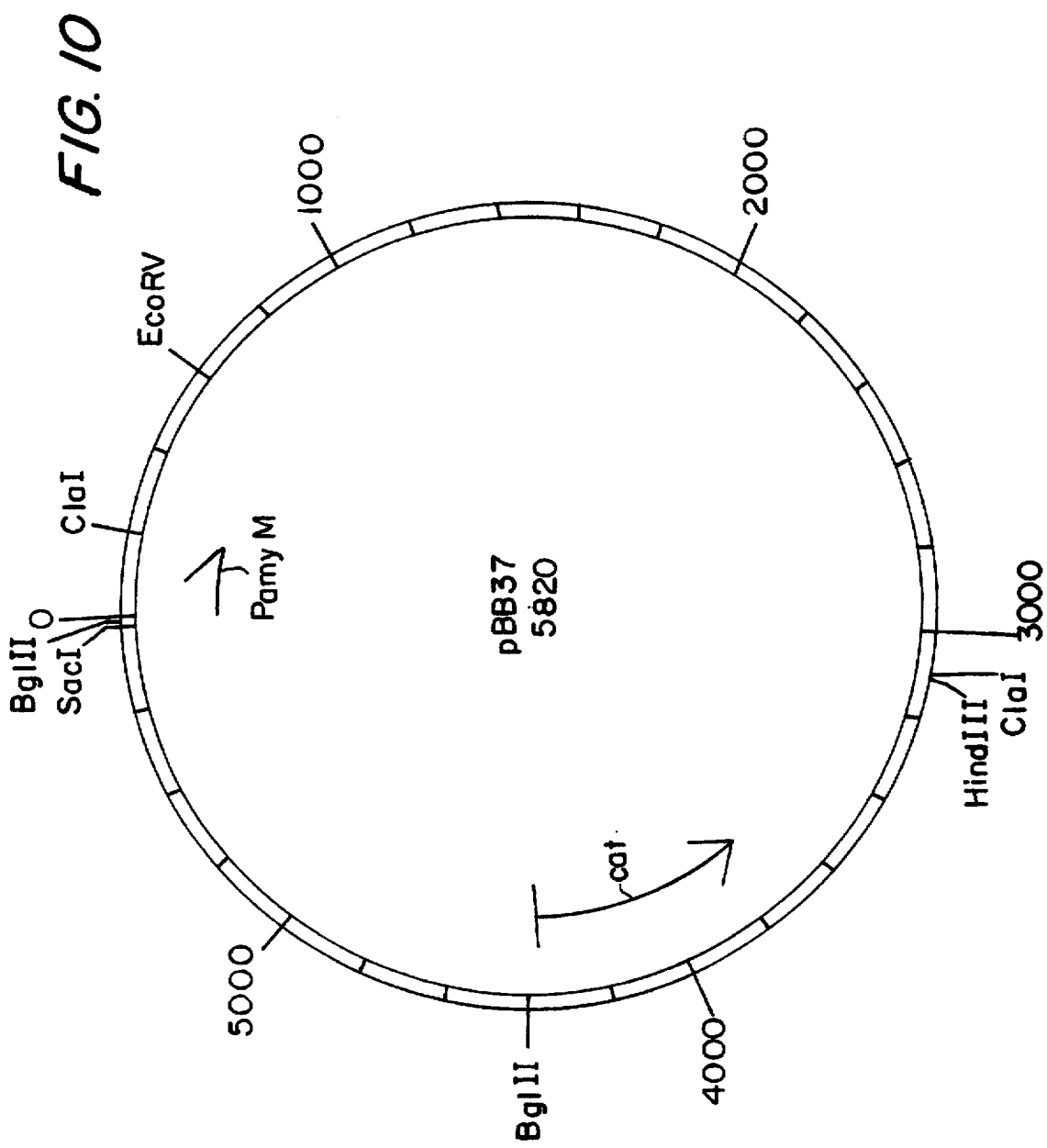
Figure 11:
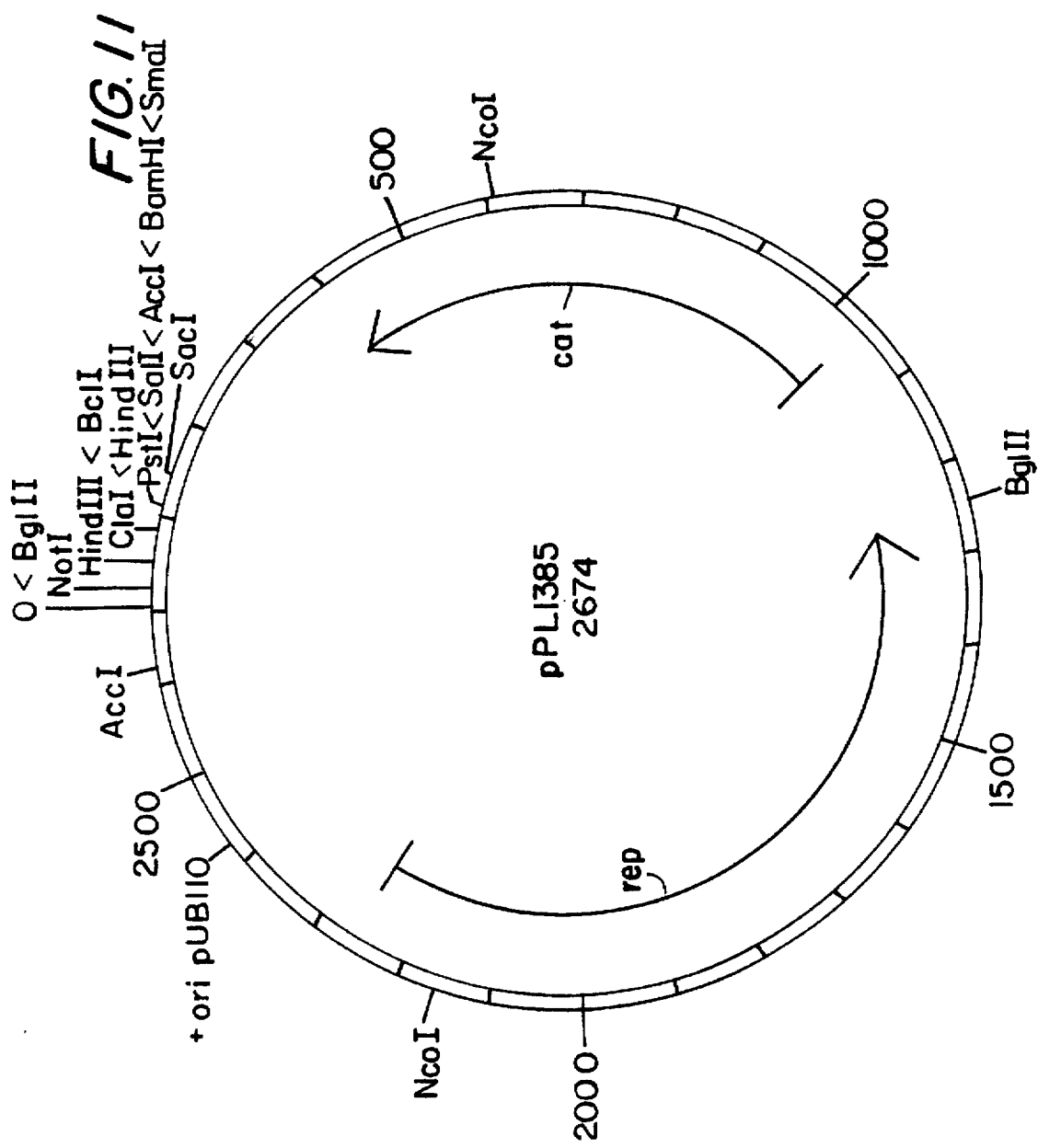
Figure 12:
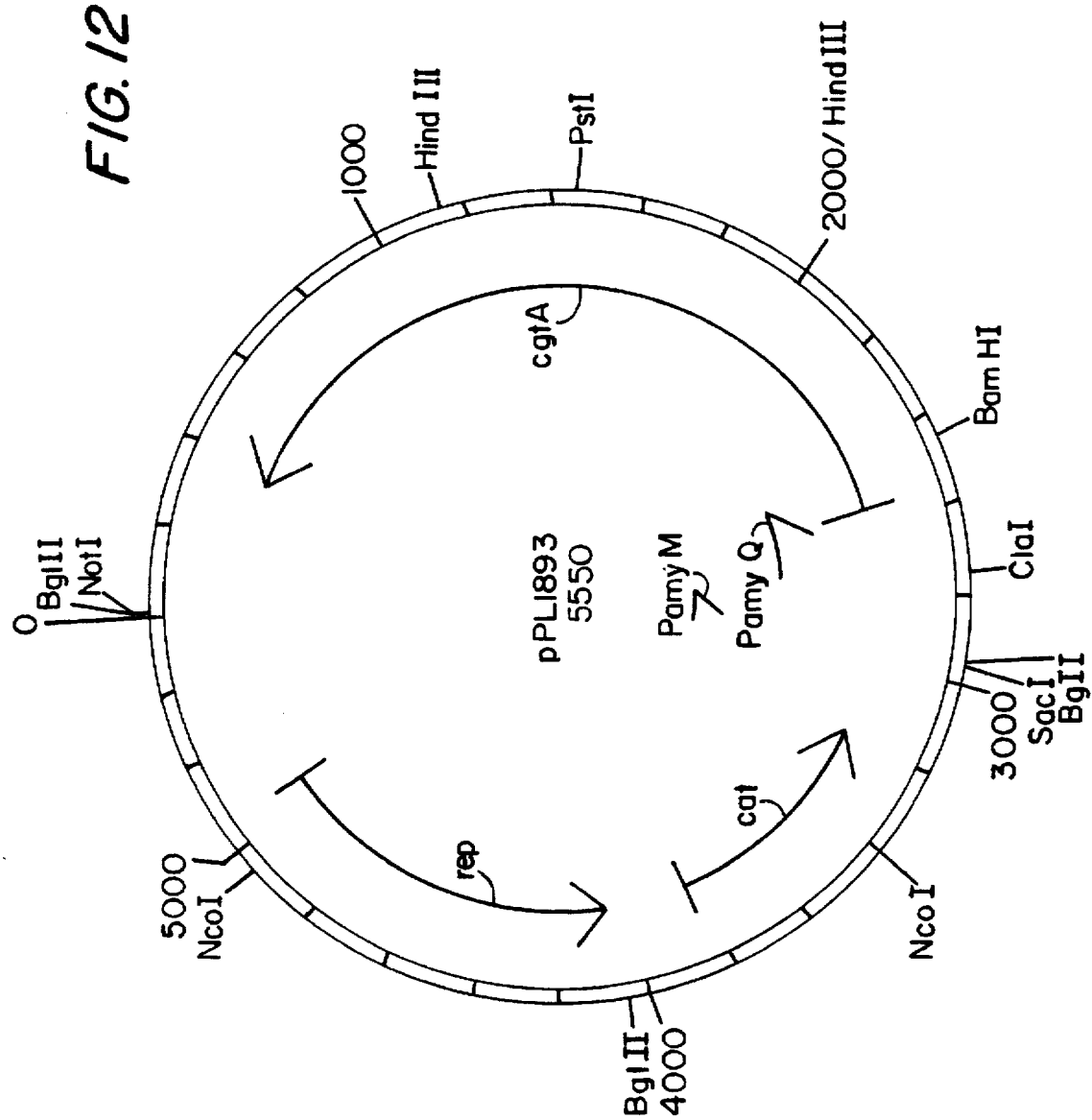
Figure 13:
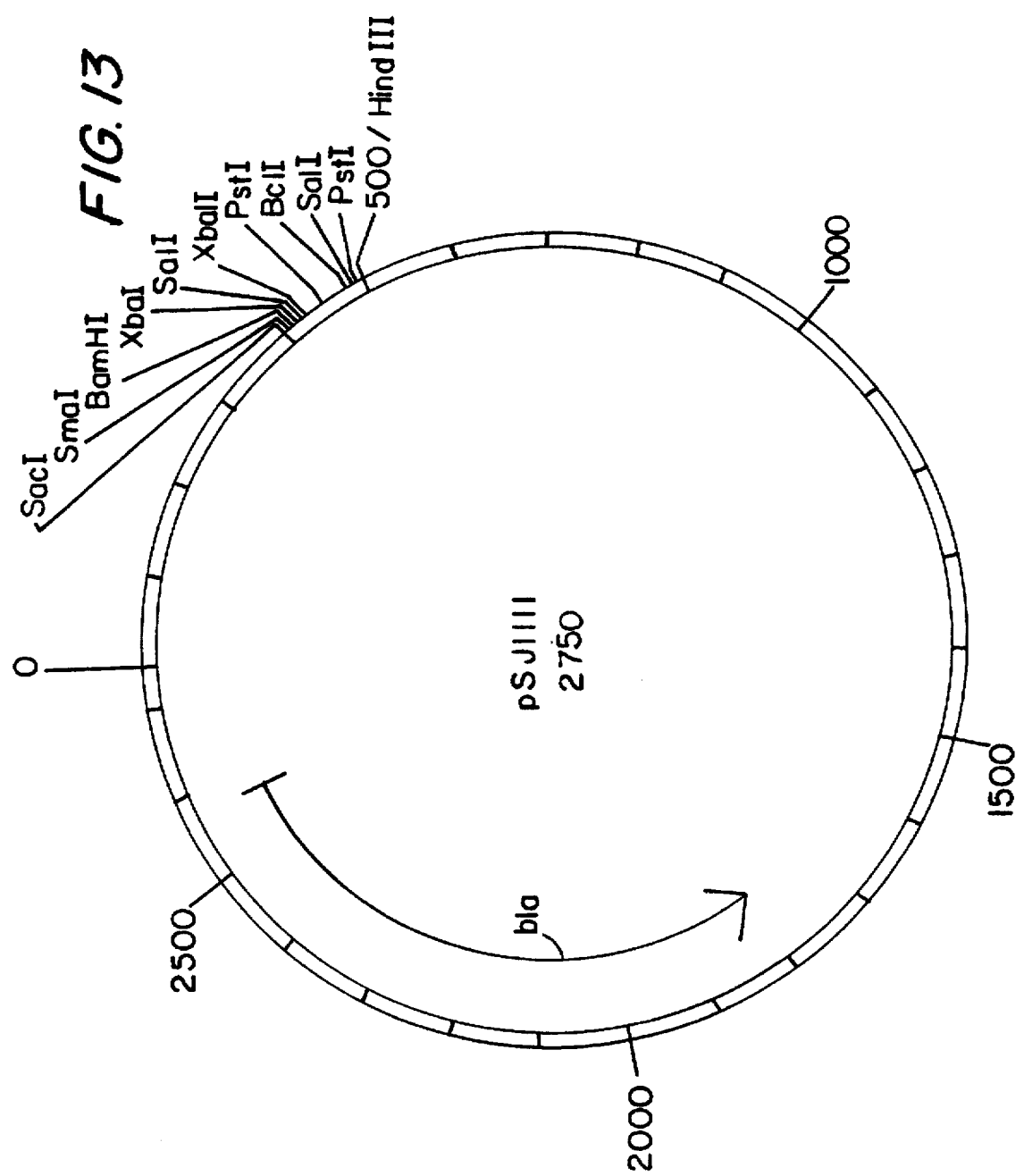
Figure 14:
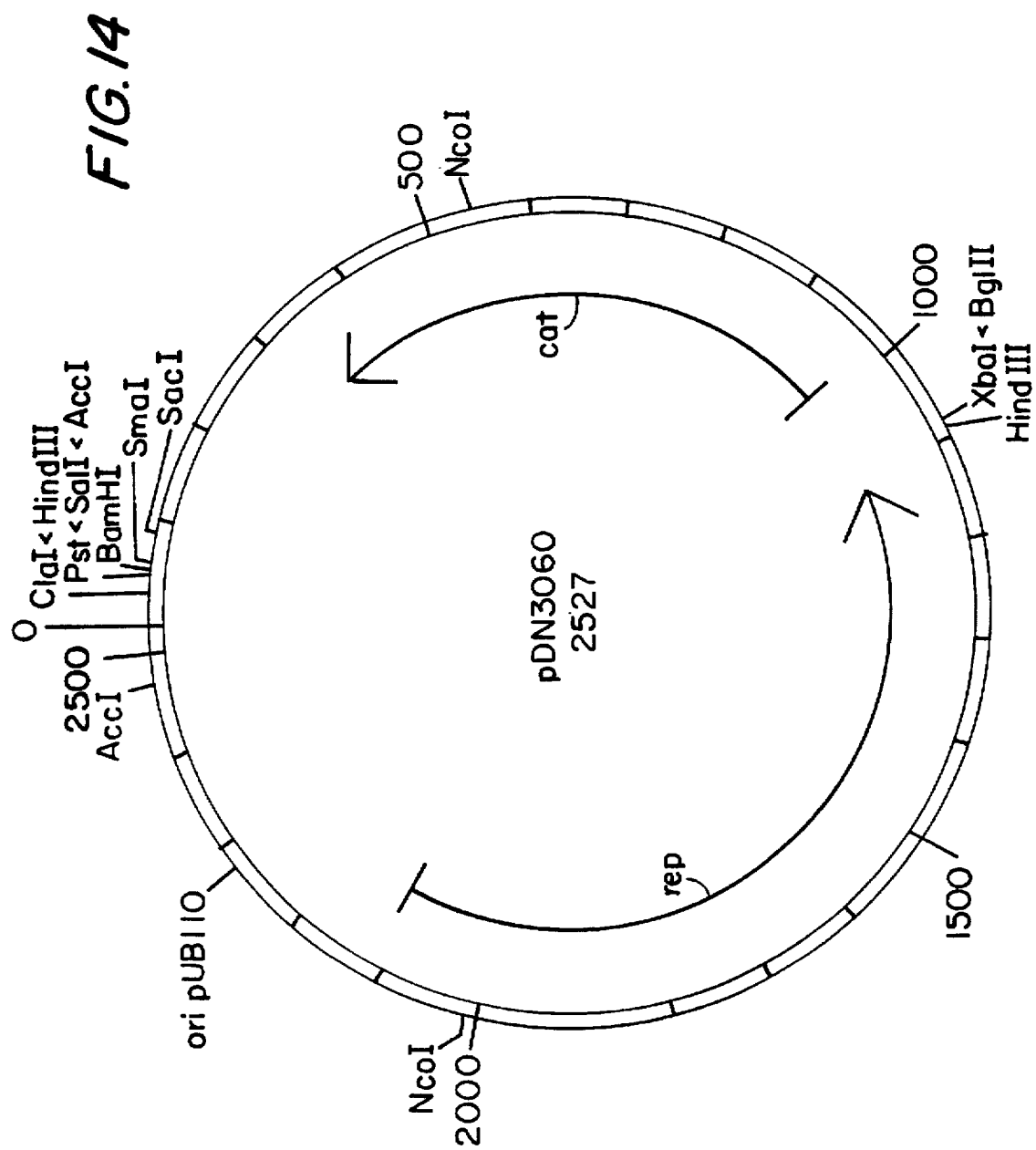
Figure 15:
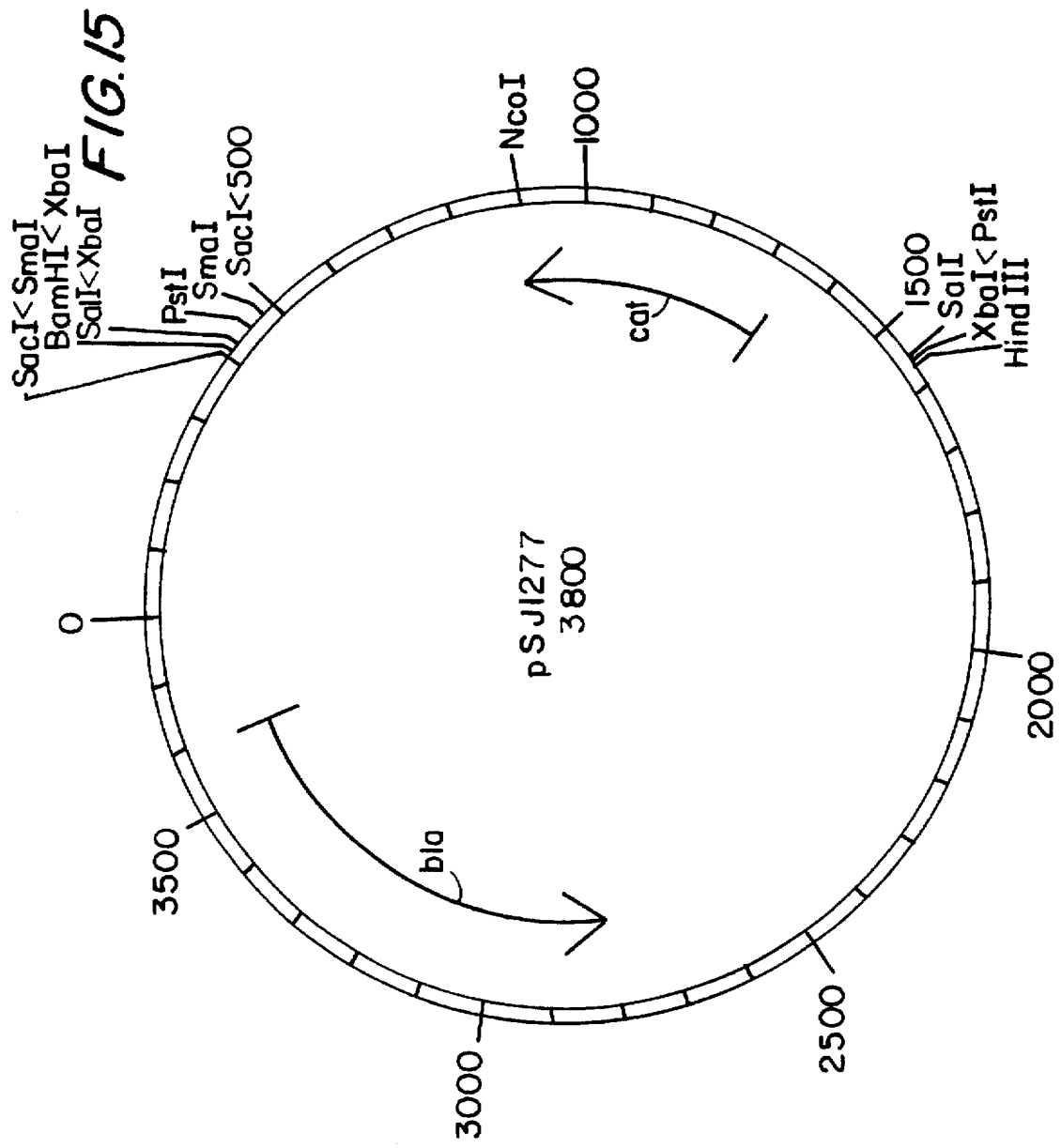
Figure 16:
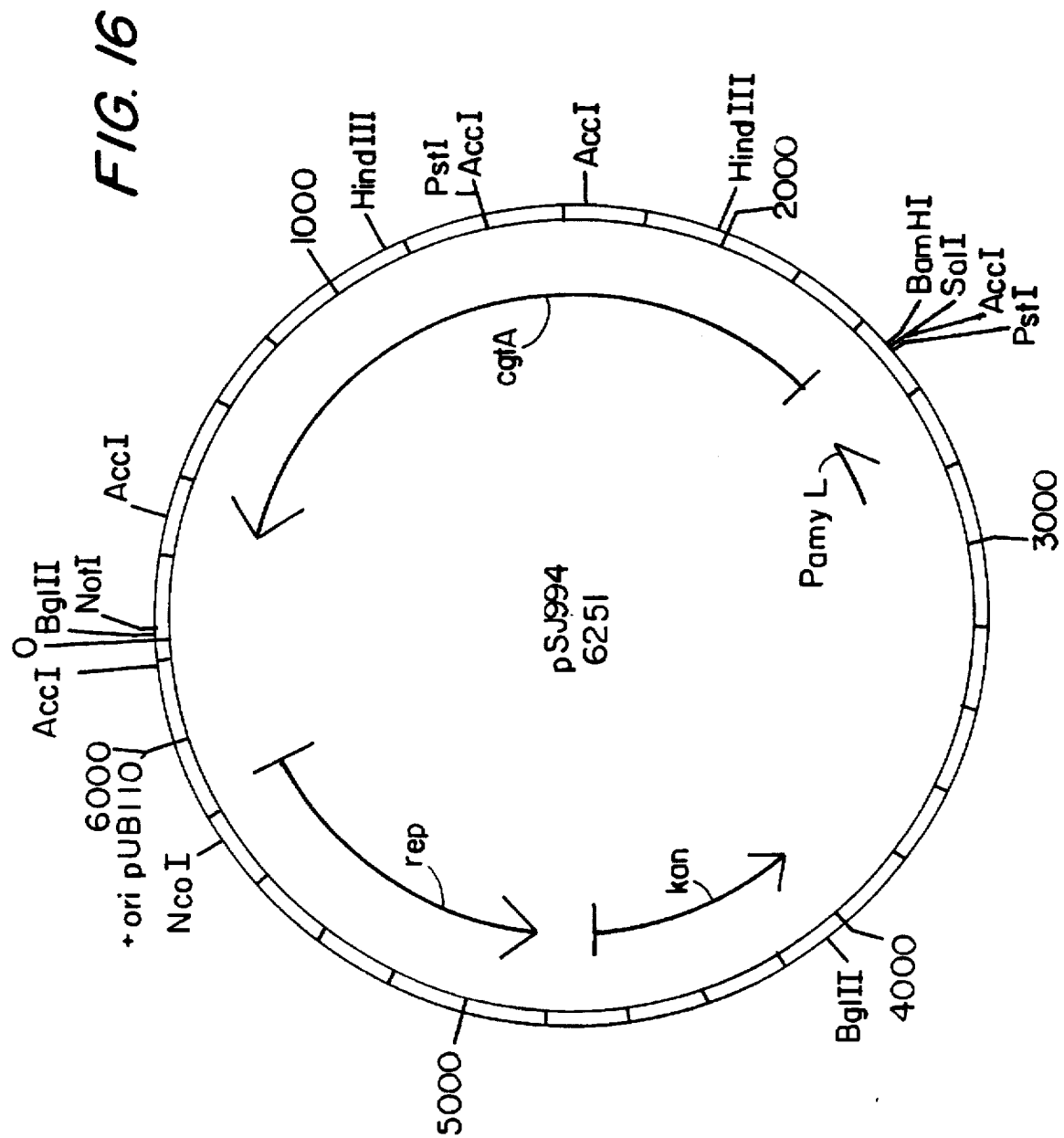
Figure 17:
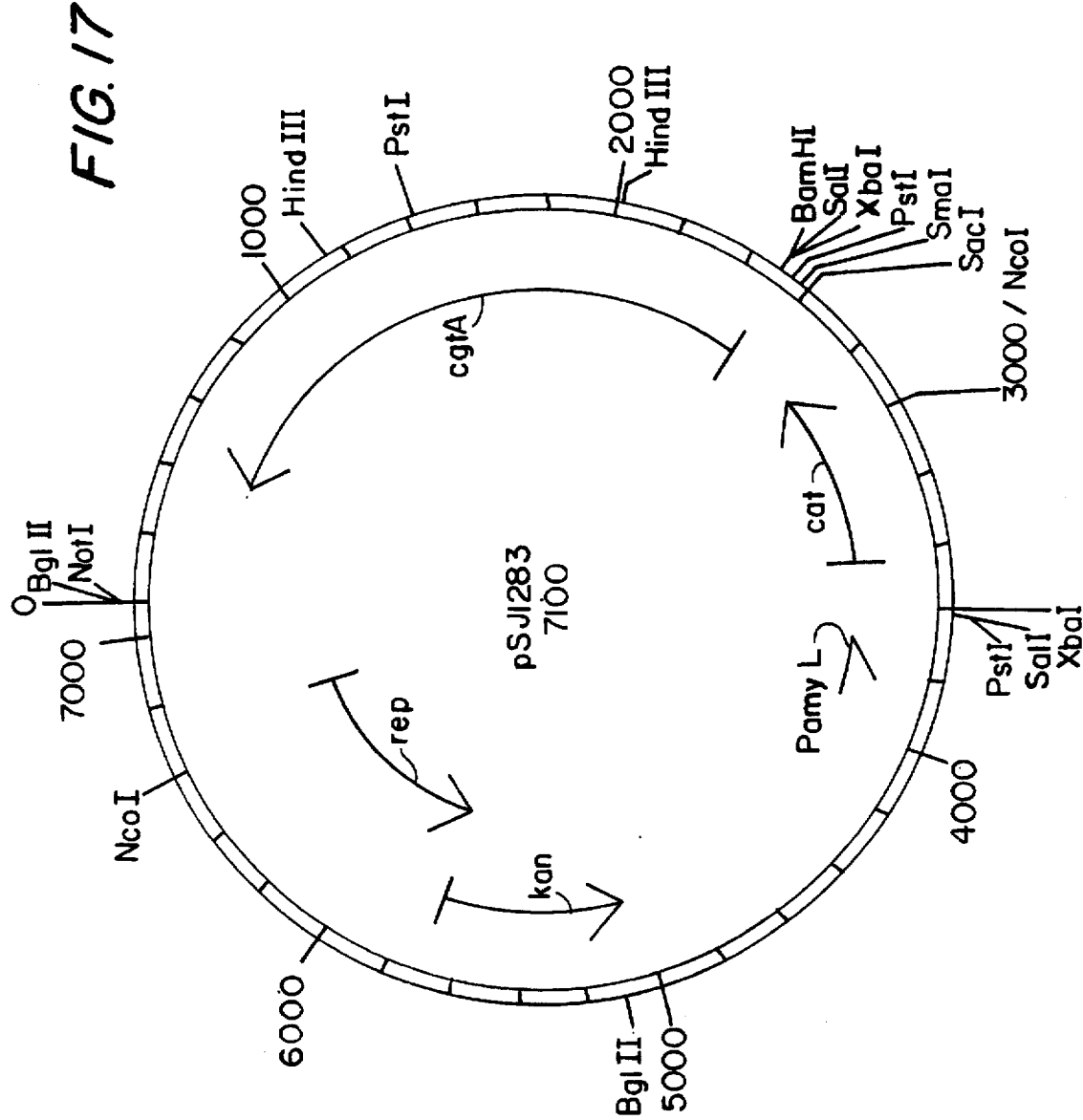
Figure 18:
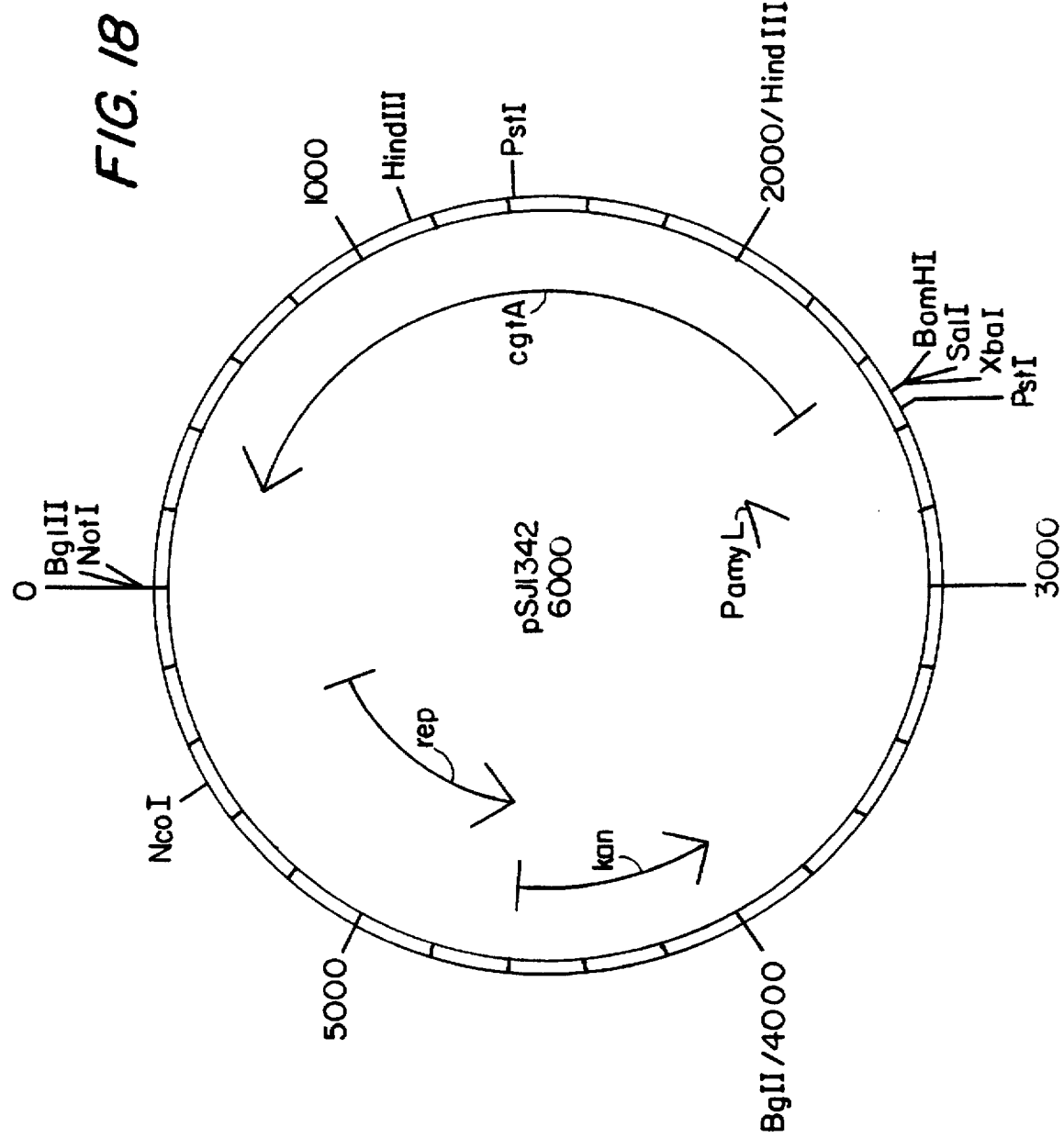
Figure 19:
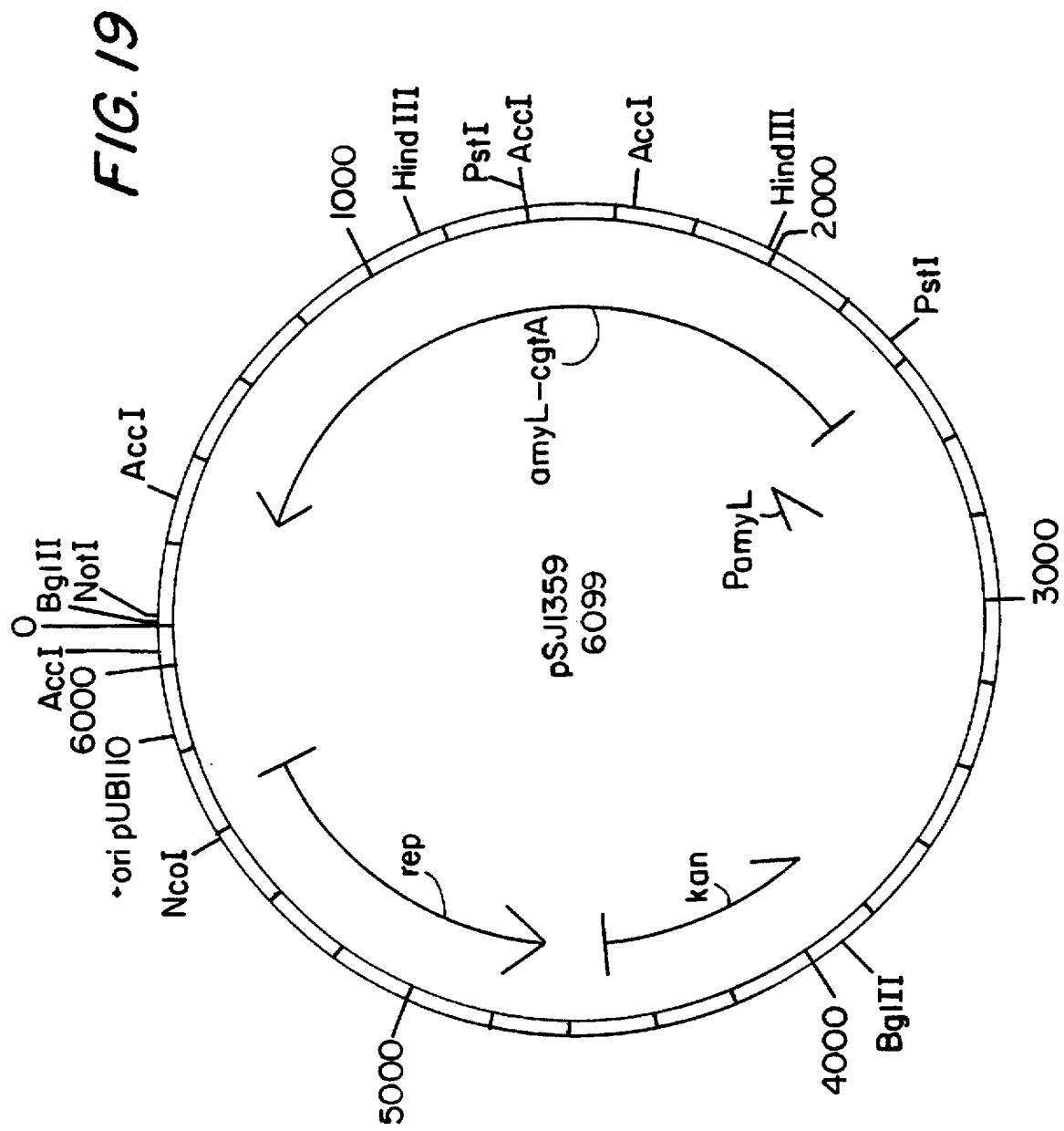
Figure 20:
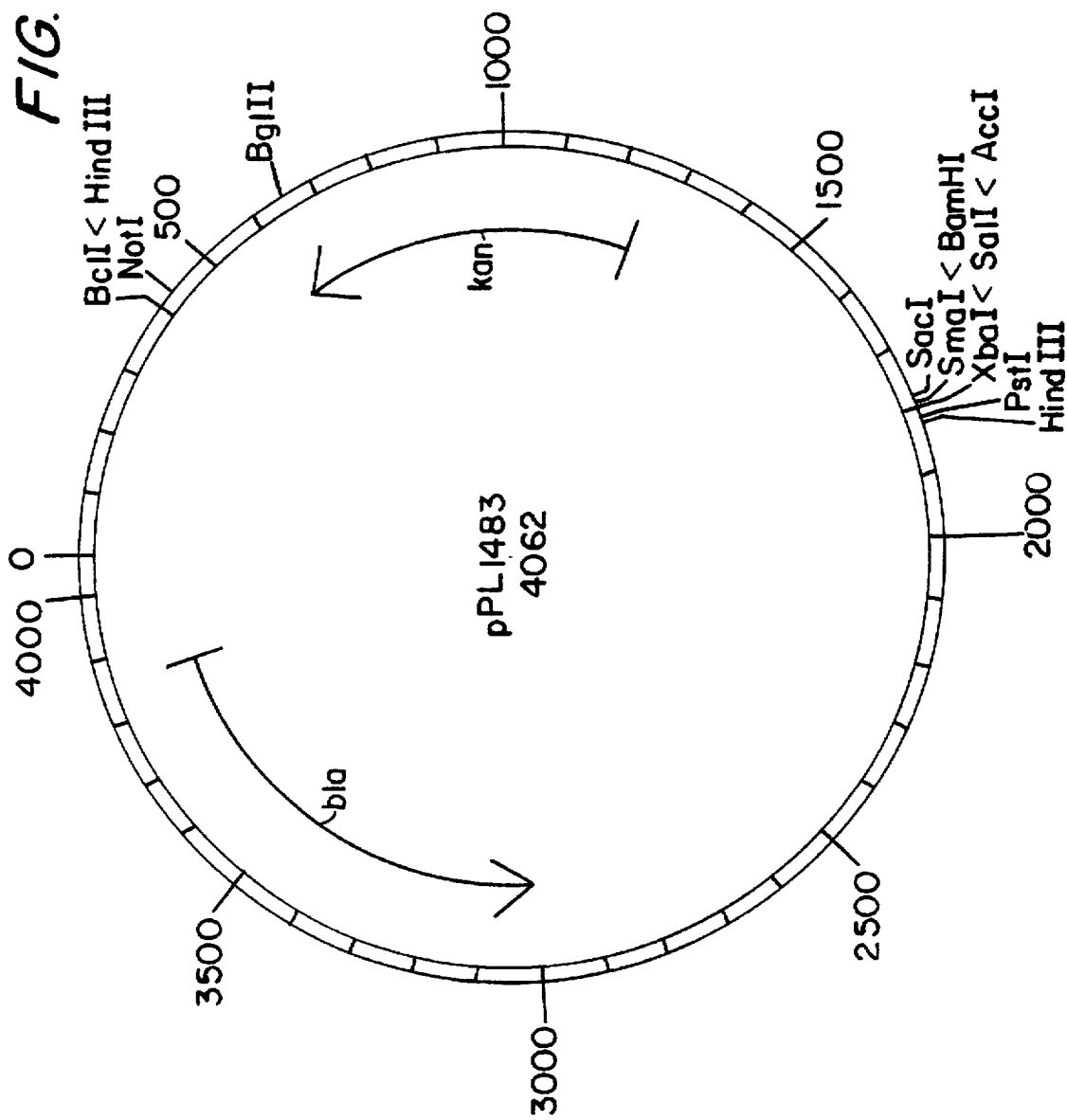
Figure 21:
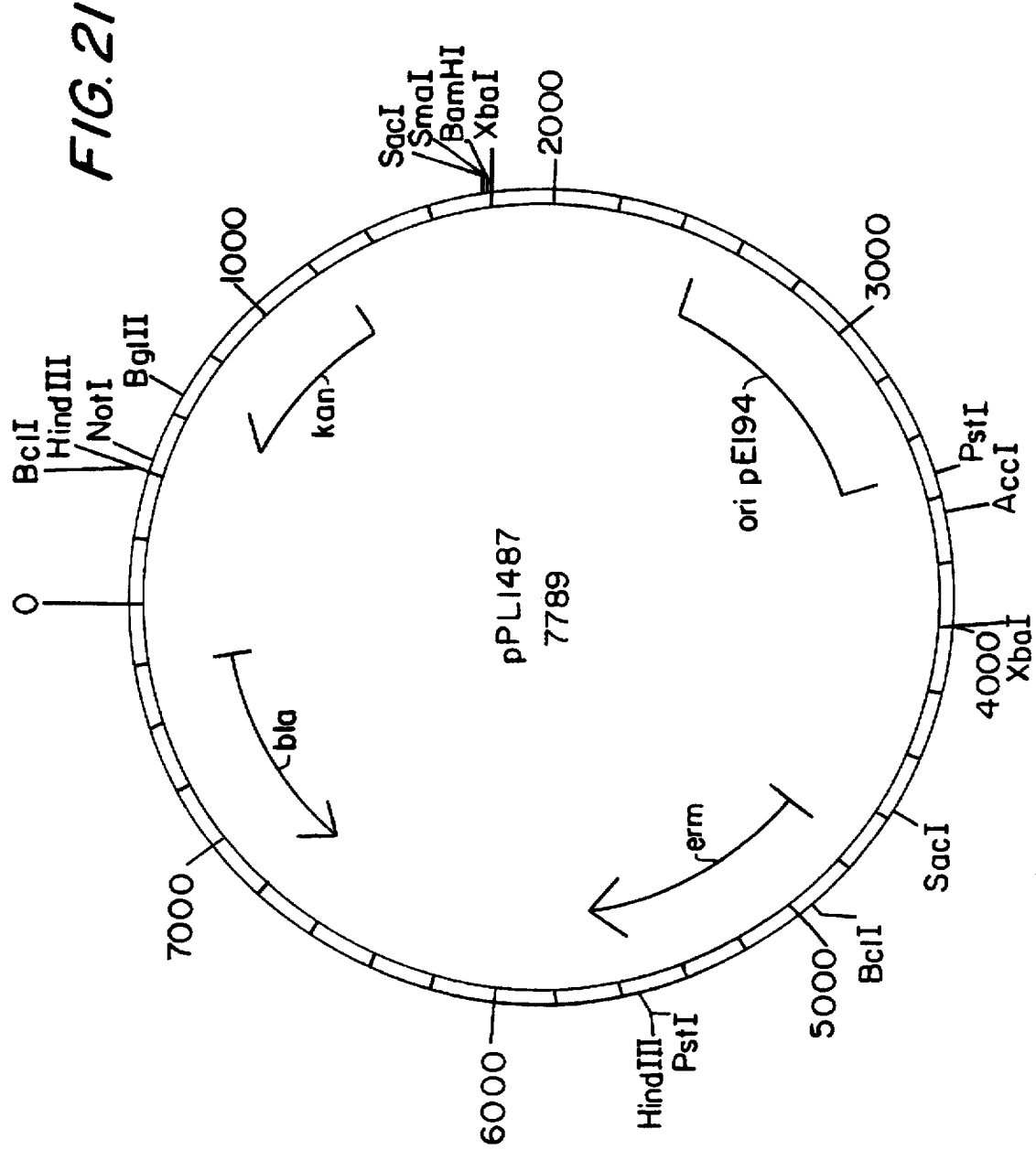
Figure 22:
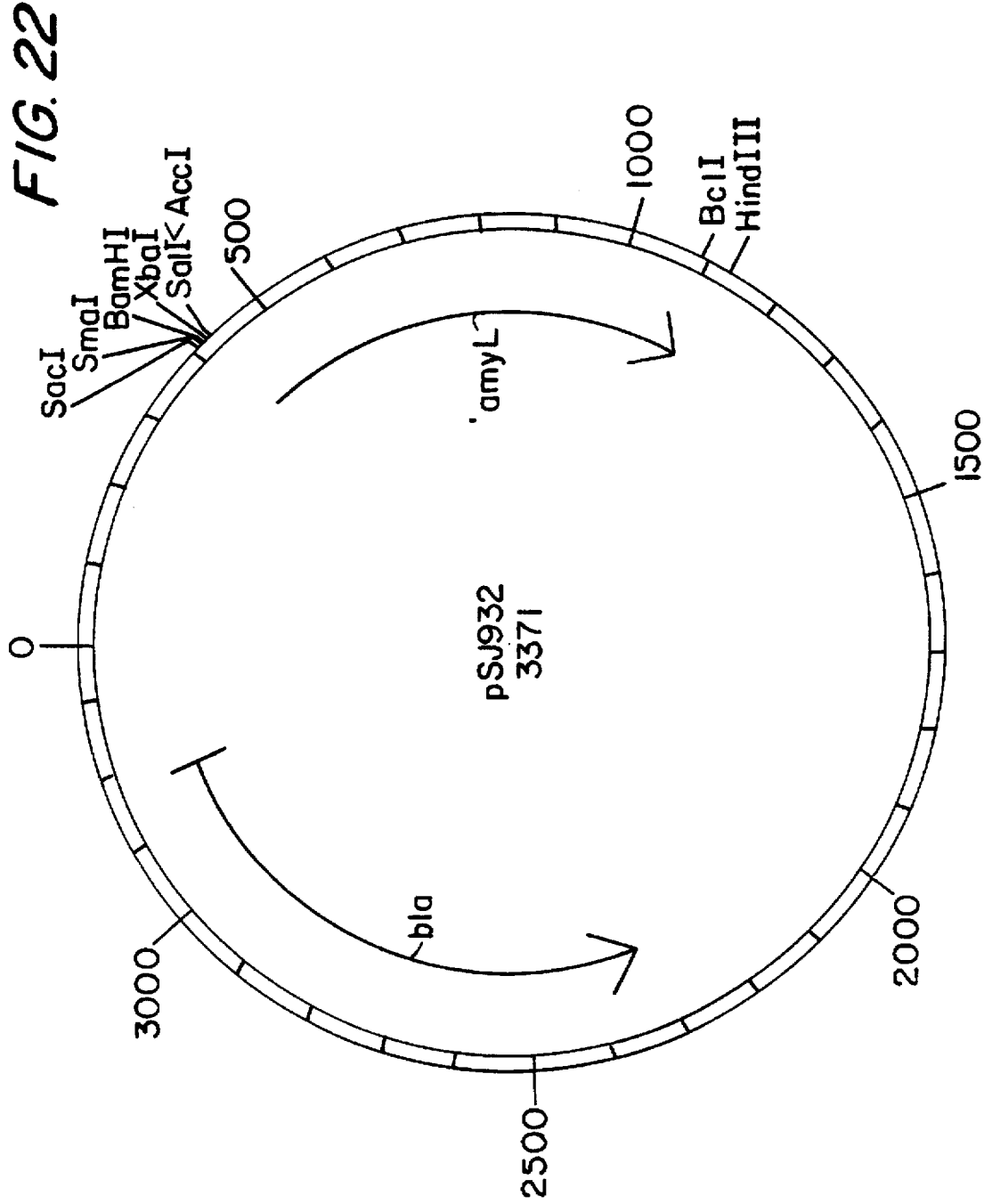
Figure 23:
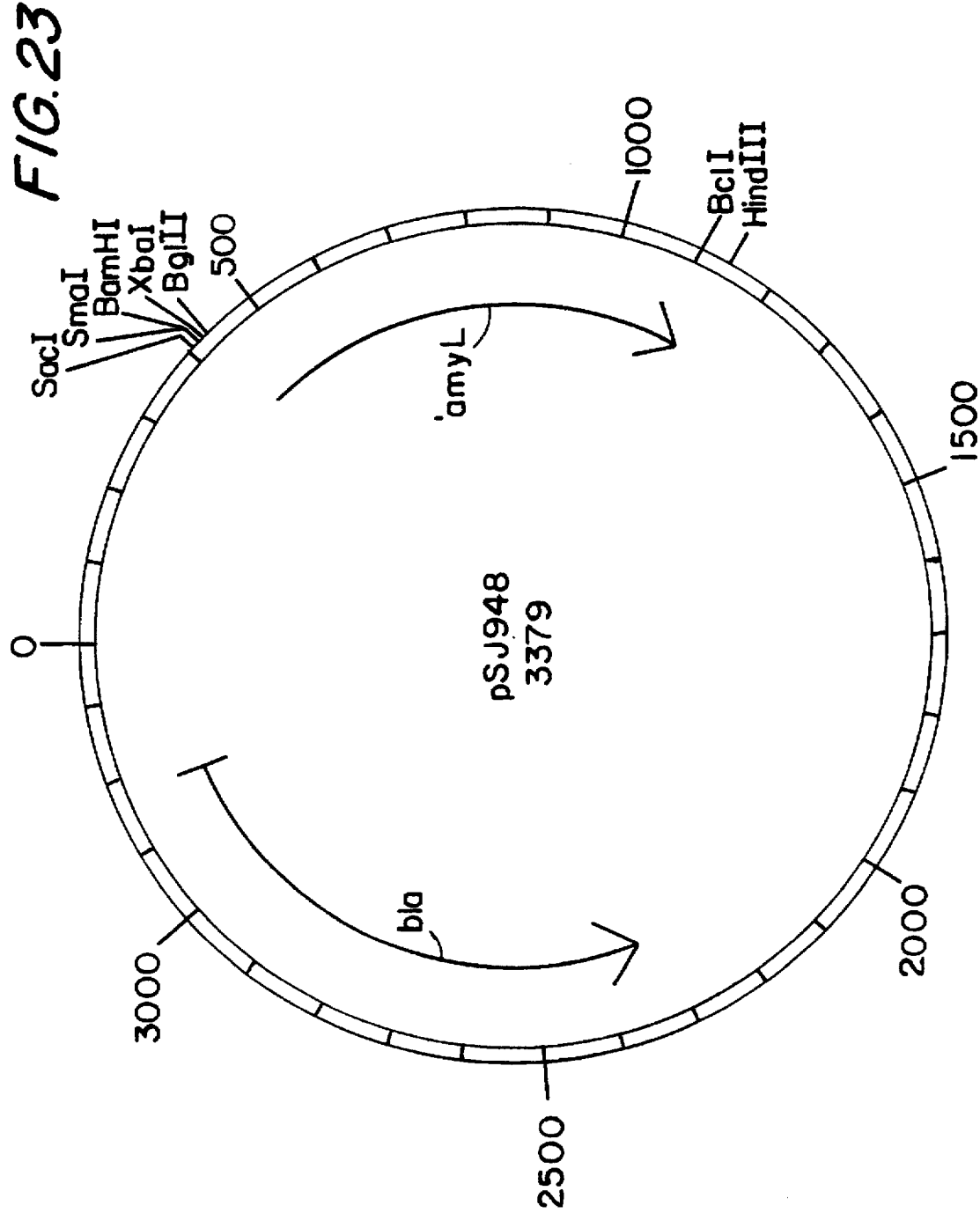
Figure 24:
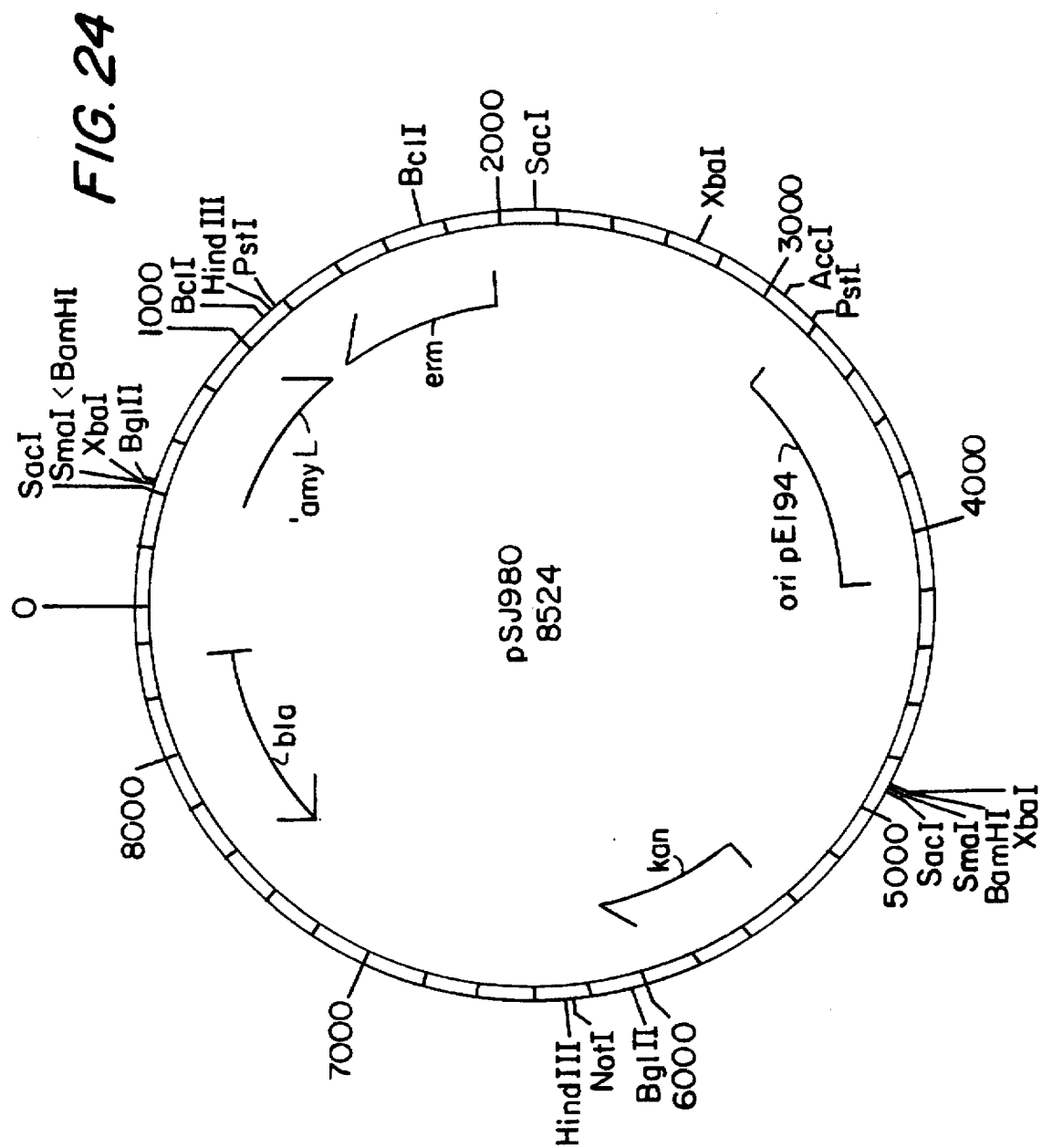
Figure 25:
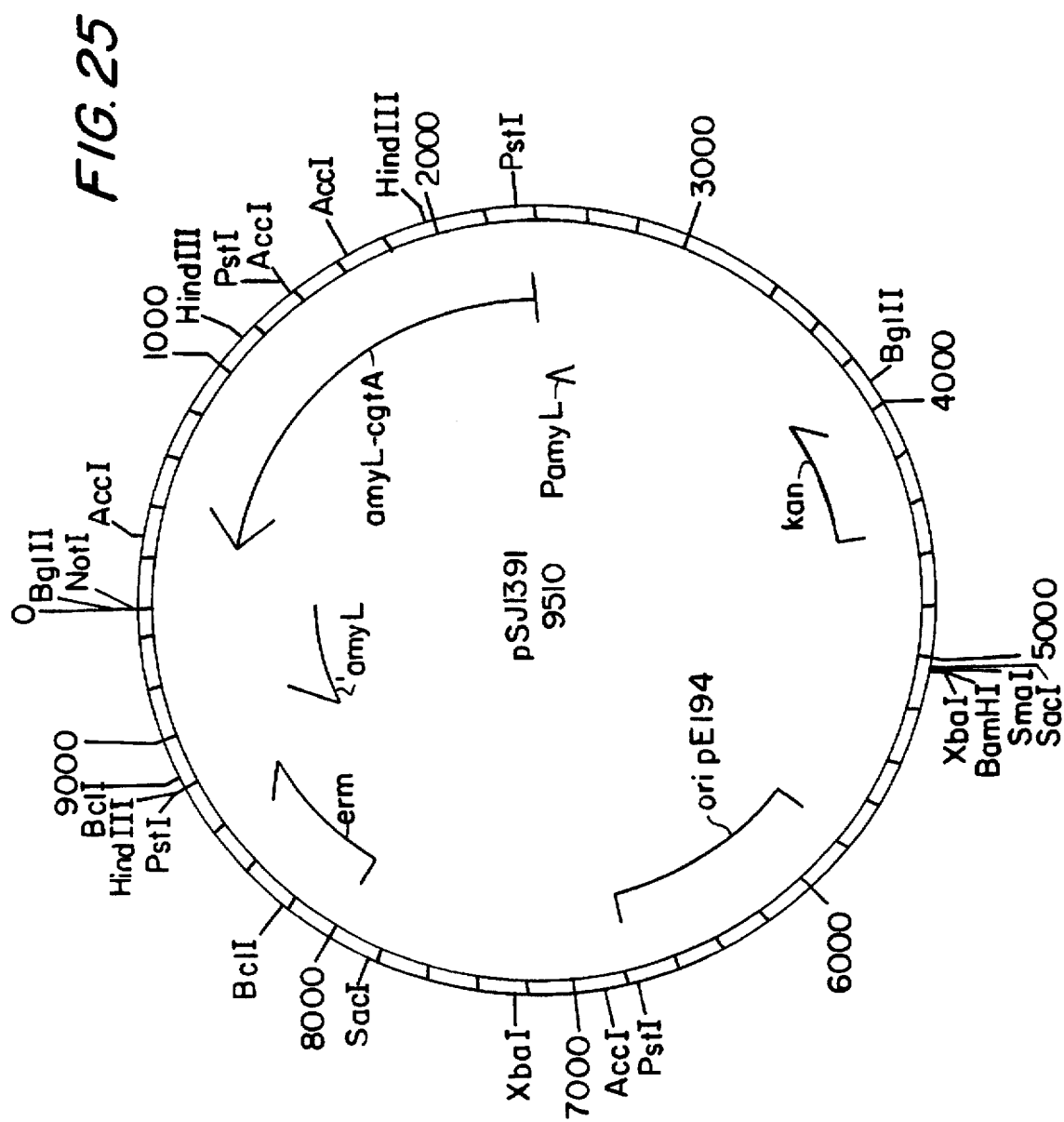
Figure 28:
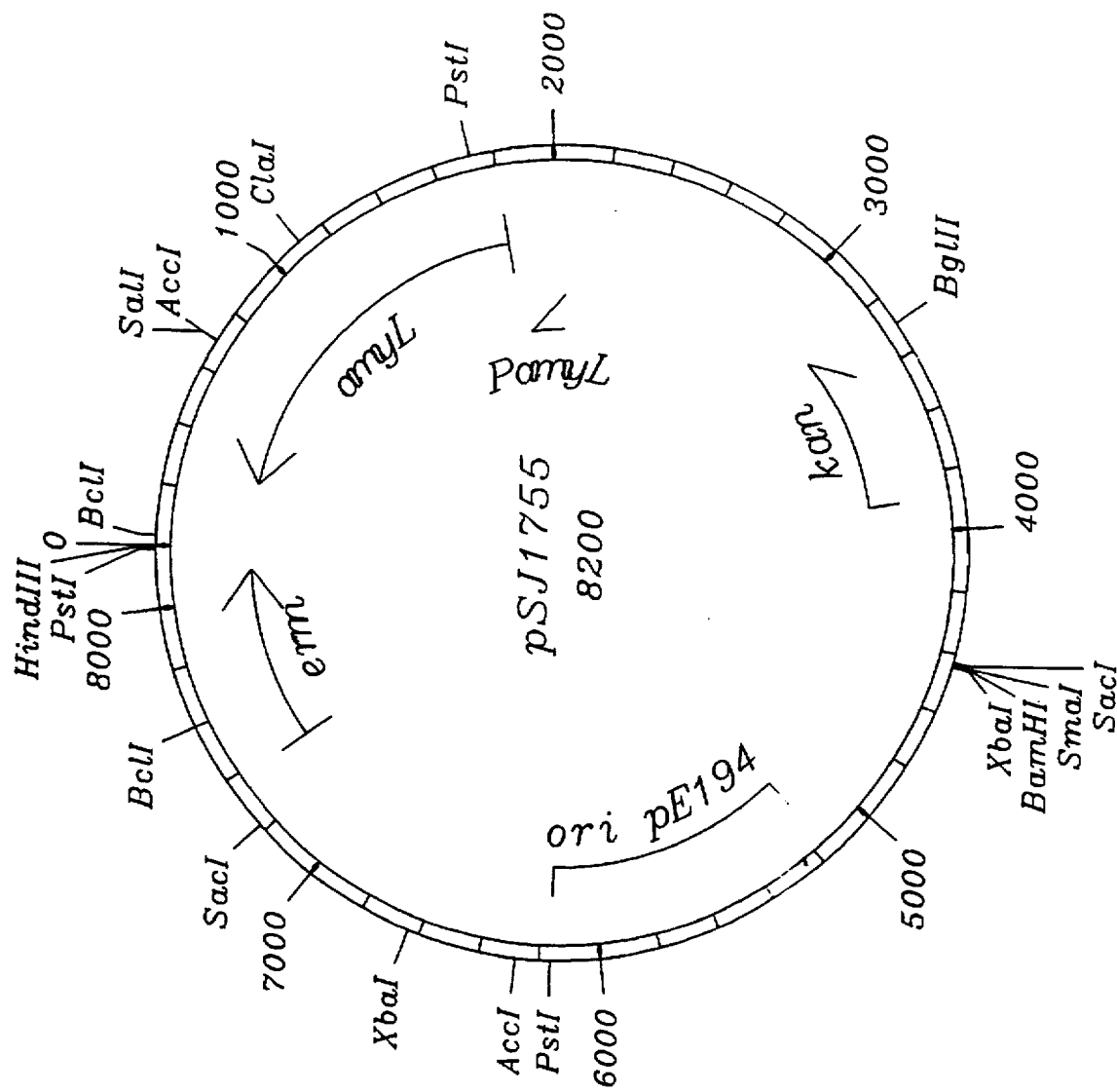

FIG. 1 is a restriction map of plasmid pNV601;
FIG. 2 is a restriction map of plasmid pPL1878;
FIG. 3 is a restriction map of plasmid pPL1419;
FIG. 4 is a restriction map of plasmid pPL1489;
FIG. 5 is a restriction map of plasmid pPL1540;
FIG. 6 is a restriction map of plasmid pDN3000;
FIG. 7 is a restriction map of plasmid pPL1759;
FIG. 8 is a restriction map of plasmid pPL1892;
FIG. 9 is a restriction map of plasmid pPL1796;
FIG. 10 is a restriction map of plasmid pBB37;
FIG. 11 is a restriction map of plasmid pPL1385;
FIG. 12 is a restriction map of plasmid pPL1893;
FIG. 13 is a restriction map of plasmid pSJ1111;
FIG. 14 is a restriction map of plasmid pDN3060;
FIG. 15 is a restriction map of plasmid pSJ1277;
FIG. 16 is a restriction map of plasmid pSJ994;
FIG. 17 is a restriction map of plasmid pSJ1283;
FIG. 18 is a restriction map of plasmid pSJ1342;
FIG. 19 is a restriction map of plasmid pSJ1359;
FIG. 20 is a restriction map of plasmid pPL1483;
FIG. 21 is a restriction map of plasmid pPL1487;
FIG. 22 is a restriction map of plasmid pSJ932;
FIG. 23 is a restriction map of plasmid pSJ948;
FIG. 24 is a restriction map of plasmid pSJ980;
FIG. 25 is a restriction map of plasmid pSJ1391;
FIG. 26 is a schematic presentation of the exchange, by homologous recombination, between the chromosomal α-amylase gene and the amyL-cgtA fusion gene carried on plasmid pSJ1391;
FIG. 27 is a schematic presentation of the in vivo recombination between the 5' ends of the mature parts of cgtA; and
FIG. 28 is a restriction map of plasmid pSJ1755.

The invention is further illustrated in the following examples which are not in any way intended to limit the scope of the invention as claimed.

EXAMPLE

General Methods

The experimental techniques used to construct the plasmids were standard techniques within the field of recombinant DNA technology, cf. T. Maniatis et al., Molecular Cloning: A Laboratory Manual, Cold Spring Harbor, N.Y., 1982.

Restriction endonucleases were purchased from New England Biolabs and Boehringer Mannheim and used as recommended by the manufacturers. T4 DNA ligase was purchased from New England Biolabs and used as recommended by the manufacturer.

Preparation of vector DNA from all strains was conducted by the method described by Kieser, 1984.

Transformation of E. coli:

Cells of E. coli were made competent and transformed as described by Mandel and Higa, 1970.

Transformation of B. subtilis:

Competent cells were prepared and transformed as described by Yasbin et al., 1975.

Transformation of B. licheniformis:

Plasmids were introduced into B. licheniformis by polyethylene glycol-mediated protoplast transformation as described by Akamatzu, 1984.

CGTase-producing colonies of either E. coli, B. subtilis or B. licheniformis were identified by plating transformants on LB agar plates supplemented with 1% soluble starch. After incubation at either 37° C. or 30° C. overnight, plates were stained by iodine vapour to show hydrolysis zones produced by the action of the CGTase on the starch.

Media

| BPX: | Potato starch | 100 g/l |
|---|---|---|
| | Barley flour | 50 g/l |
| | BAN 5000 SKB | 0.1 g/l |
| | Sodium caseinate | 10 g/l |
| | Soy Bean Meal | 20 g/l |
| | $Na_2HPO_4$, 12 $H_2O$ | 9 g/l |
| | Pluronic | 0.1 g/l |
| LB agar: | Bacto-tryptone | 10 g/l |
| | Bacto yeast extract | 5 g/l |
| | NaCl | 10 g/l |

1. Cloning of a Thermoanaerobacter sp. CGTase gene into *Bacillus subtilis*

The construction of the *E. coli* plasmid pNV601 (FIG. 1), carrying the Thermoanaerobacter sp. ATCC 53627 CGTase gene referred to in the following as cgtA, is disclosed in WO 89/03421. The *B. subtilis* plasmid pPL1878 (FIG. 2), containing the cgtA gene, is disclosed in WO 91/09129. It was constructed as follows:

pNV601 was digested partially with Sau3A, then religated and transformed into *E. coli* SCS1 (frozen competent cells purchased from Stratagene, Ja Jolla, Calif.), selecting for ampicillin resistance (200 µg/ml). One CGTase positive colony was PL1419, containing pPL1419 (FIG. 3). Plasmid pPL1419 was partially digested with Sau3A, and fragments ligated to BglII digested pPL1489 (FIG. 4). One CGTase positive, ampicillin resistant (200 µg/ml) *E. coli* SCS1 transformant contained pPL1540 (FIG. 5). pPL1489 was derived from plasmid pKK233-2 (purchased from Pharmacia LKB Biotechnology) by insertion of a synthetic DNA linker between the PstI and HindIII sites in pKK233-2. This linker was the PstI-HindIII fragment from pDN3000 (FIG. 6; WO 91/09129, Diderichsen et al., 1990). pPL1540 was digested with HaeII and SphI, and the 2.4 kb fragment containing the cgtA gene was inserted into HaeII+SphI digested plasmid pDN1380 (Diderichsen and Christiansen, 1988). A CGTase positive, chloramphenicol resistant (6 µg/ml) transformant of *B. subtilis* DN1885 (Diderichsen et al., 1990) contained pPL1878.

2. Construction of an α-amylase/CGTase fusion gene

Cloning of the *Bacillus licheniformis* α-amylase gene, amyL, resulting in plasmid pDN1981, is described by Jorgensen et al., 1990.

In plasmid pPL1759 (FIG. 7), the PstI-HindIII fragment of pDN1981 has been replaced by the PstI-HindIII multilinker fragment from pDN3000 (FIG. 6). It has retained the amyL promoter and most of the signal peptide coding sequence.

Plasmid pPL1892 (FIG. 8) was constructed by insertion of the cgtA gene excised from pPL1878 on a 2.4 kb SalI-NotI fragment into SalI+NotI digested pPL1759, and transformation of DN1885 to kanamycin resistance (10 µg/ml).

Plasmid pPL1796 (FIG. 9) was constructed by insertion of a 0.5 kb SacI-EcoRV fragment from pBB37 (FIG. 10; Jorgensen, P. et al., 1991) into SacI+SmaI digested pPL1385 (FIG. 11; Diderichsen et al., 1990), and transformation of DN1885 to chloramphenicol resistance (6 µg/ml).

Plasmid pPL1893 (FIG. 12) was constructed by insertion of the CGTase gene excised from pPL1878 on a 2.4 kb BamHI-NotI fragment into BamHI+NotI digested pPL1796, and transformation of DN1885 to chloramphenicol resistance (6 µg/ml).

The in vivo genetic engineering technique (Jorgensen et al., 1990), by which two DNA sequences contained on the same plasmid and sharing a homologous region can be fused together by recombination between the homologous regions in vivo (see FIG. 27) was used to construct a fusion between the amyL and the cgtA genes, in which the cgtA signal peptide coding sequence had been precisely replaced by the signal peptide coding sequence of the amyL gene.

To this end, the following oligonucleotide linker was synthesized and ligated into SalI digested pUC19 (Yanish-Perron et al., 1985), giving pSJ1111 (FIG. 13) upon transformation of *E. coli* SJ2 (Diderichsen et al., 1990) and selection for ampicillin resistance (200 µg/ml):

```
                3' end of amyL signal peptide
                      coding region
         SalI                              PstI
5'- TCGACTGATCACTTGCTGCCTCATTCTGCAGCAGCGGCG-
3'-     GACTAGTGAACGACGGAGTAAGACGTCGTCGCCGC- 5' end of cgtA mature protein
coding region
                     XbaI       SalI
GCACCGGATACTTCAGTTTCTCTAGAG       -3' (SEQ ID NO: 7)
CGTGGCCTATGAAGTCAAAGAGATCTCAGCT- 5' (SEQ ID NO: 3)
```

The pC194 (Horinouchi and Weisblum, 1982) derived chloramphenicol resistance gene, cat, was excised from pDN3060 (FIG. 14; WO 91/09129) as a 1.1 kb BamHI-BglII fragment and inserted into BclI digested pSJ1111, giving pSJ1277 (FIG. 15) upon transformation of *E. coli* SJ 6 (Diderichsen et al., 1990) and selection for ampicillin (200 µg/ml) and chloramphenicol (6 µg/ml) resistance.

pSJ994 (FIG. 16) was constructed by ligation of the 0.6 kb NotI-NcoI fragment from pPL1893 to the 5.4 kb NotI-NcoI fragment from pPL1892, and transformation into *B. subtilis* DN1885, selecting for kanamycin resistance (10 µg/ml).

pSJ1283 (FIG. 17) was constructed by ligation of the 1.1 kb SalI fragment from pSJ1277 to SalI digested pSJ994, and transformation into DN1885, selecting for kanamycin (10 µg/ml) and chloramphenicol (6 µg/ml) resistance.

pSJ1342 (FIG. 18) was constructed by deletion of the 1.1 kb PstI fragment from pSJ1283, and transformation into DN1885, selecting for kanamycin resistance (10 µg/ml).

pSJ1359 (FIG. 19) was constructed by the actual in vivo recombination from pSJ1342. There is homology between the start of the mature part of the CGTase gene and part of the synthetic oligonucleotide extending between PstI and SalI on pSJ1342. If the plasmid undergoes a recombination event between these two homologous regions, the unique sites for XbaI, SalI and BamHI will be deleted.

A batch of pSJ1342 prepared from host strain DN1885 was thoroughly digested with BamHI, XbaI and SalI, and the digested plasmid was directly (i.e. without ligation) transformed into competent cells of DN1885, selecting for kanamycin resistance (10 µg/ml). This procedure strongly enriches for recombined plasmids, as linearized plasmid monomers are unable to transform *B. subtilis* competent cells (Mottes et al., 1979). Recombined plasmids would not be cleaved by the restriction enzymes, and thus exist as a mixture of monomeric and oligomeric forms well able to transform competent *B. subtilis* cells. One transformant thus obtained contained pSJ1359. This plasmid contains the origin of replication of pUB110 (Lacey and Chopra, 1974, Gryczan et al., 1978, McKenzie et al., 1986), the pUB110 Rep protein gene, the kanamycin resistance gene, and the *B. licheniformis* α-amylase (amyL) promoter and signal peptide coding region perfectly fused to the DNA encoding the mature part of the CGTase from Thermoanaerobacter sp. ATCC 53627.

3. Construction of a chromosomal integration vector

A 1.4 kb BamHI fragment containing the pUB110 kanamycin resistance gene (kan) was excised from plasmid pDN2904 (WO 91/09129), ligated to BglII digested pDN3000 (FIG. 6), transformed into *E. coli* SCS1 selecting ampicillin resistance (100 µg/ml), and pPL1483 (FIG. 20) was recovered from one such transformant.

This plasmid was then combined with a Bacillus vector temperature sensitive for replication, plasmid pE194

(Horinouchi and Weisblum, 1982b). pPL1483 was digested with AccI, pE194 digested with ClaI, the two linearized plasmids mixed, ligated, and transformed into *B. subtilis* DN1885 selecting kanamycin resistance (10 µg/ml) at 30° C. One such transformant contained pPL1487 (FIG. 21).

A 3'-terminal fragment of the amyL gene was excised from plasmid pDN1528 (Jorgensen, S. et al., 1991) as a 0.7 kb SalI-HindIII fragment, ligated to SalI+HindIII digested pUC19, and transformed to *E. coli* SJ2, selecting for ampicillin resistance (200 µg/ml). One such transformant contained pSJ932 (FIG. 22).

Plasmid pSJ948 (FIG. 23) was obtained by insertion of a BglII linker into HindII digested pSJ932, once more selecting for ampicillin resistance (200 µg/ml) upon transformation of SJ2.

pSJ980 (FIG. 24) was constructed by ligation of the 5.1 kb HindIII fragment of pPL1487 to HindIII digested pSJ948, selecting for kanamycin resistance (10 µg/ml) in *B. subtilis* DN1885 at 30° C.

Finally, pSJ1391 (FIG. 25) was constructed by ligation of the 4.0 kb BglII fragment of pSJ1359 to the 5.6 kb BglII fragment of pSJ980, selecting for kanamycin resistance (10 µg/ml) in DN1885 at 30° C. This plasmid contains, on a vector temperature-sensitive for replication and conferring resistance to kanamycin and erythromycin, the promoter and upstream region (about 0.4 kb) from the *B. licheniformis* α-amylase gene (amyL), the α-amylase/CGTase fusion gene (amyL-cgtA), and then about 0.7 kb from the 3'-region of the α-amylase gene (amyL).

4. Transfer of the fusion gene to *B. licheniformis* and integration in the chromosome An α-amylase producing strain of *B. licheniformis* was transformed with pSJ1391 by the protoplast transformation procedure (Akamatzu, 1984). One regenerating, kanamycin resistant colony was isolated, and was found to produce both α-amylase and CGTase. Production of the two enzymes can be easily distinguished by separating proteins in the culture supernatant from shake flask cultures in BPX medium (WO 91/09129) on isoelectric focusing gels (e.g. using the Pharmacia Phast system), followed by overlayering with an agarose gel containing 1% soluble starch and subsequent staining by iodine vapour. The CGTase activity was detected at pI 4.5, the α-amylase activity at pI 8.

When this transformant was analyzed for its plasmid content, it turned out that a recombination event between the incoming plasmid and the chromosome had taken place: A double recombination had exchanged the chromosomal α-amylase (amyL) gene and the plasmid borne amyL-cgtA fusion gene, so that the plasmid isolated carried the amyL gene (*B. subtilis* DN1885 transformed with this plasmid produced α-amylase) whereas the amyL-cgtA fusion gene now resided on the chromosome (FIG. 26).

By propagation in TY medium (WO 91/09129) without kanamycin, strains were isolated that had spontaneously lost their plasmid (SJ1599, SJ1603-1607).

The original *B. licheniformis* transformant was also subjected to experimental conditions to ensure chromosomal integration and subsequent excision of the plasmid, in order to promote recombination events. The transformant was plated on LB agar (WO 91/09129) with 10 µg/ml kanamycin at 50° C., individual colonies restreaked a few times at 50° C., and each then grown in successive overnight TY cultures at 30° C. without kanamycin to permit plasmid excision and loss. Kana' isolates from each original 50° C. colony were incubated in BPX shake flasks and production of either α-amylase or CGTase determined by analysis on isoelectric focusing gels as above. The plasmid free strains analyzed all produced either CGTase or α-amylase. CGTase producing isolates are e.g. SJ1561–62, 1580–83, 1586–91 and 1595.

One strain, named SJ1608, appeared to produce CGTase in larger amounts than the others.

Southern blot analysis of strains SJ1561, 1562, 1599, 1606 and 1608 confirmed that these strains have the chromosomal amyL gene replaced by the amyL-cgtA gene.

The following results were obtained by quantitation of the CGTase activity produced on incubation in BPX shake flasks for 6 days at 37° C. (results from several experiments; the variation within each group of strains was mainly due to the use of different batches of shake flasks):

| Strain | CGTase activity, arbitrary units |
| --- | --- |
| SJ1561–62, 1580–83, 1586–91, 1595, 1599, 1603–07 | 1–7.5 |
| SJ1608 | 200–275 |

5. Promoter analysis

We have investigated whether the large difference in CGTase production between strain SJ1608 and the other strains containing the amyL-cgtA gene was due to differences in the amyL promoter responsible for the CGTase expression.

The amyL promoter sequence of the *B. licheniformis* host strain is given in SEQ ID NO: 4.

The promoter region from a number of the CGTase producing *B. licheniformis* strains was amplified from chromosomal DNA by the PCR technique (Saiki et al., 1988), using as primers one oligonucleotide corresponding to pos. 204–233 reading downstream through the amyL promoter, and another oligonucleotide corresponding in sequence to the 5'-end of the DNA encoding the mature CGTase and reading upstream. The sequence of this second oligonucleotide was 5'-CCTGTTGGATTATTACTGGG-3' (SEQ ID NO: 5).

The amplified DNA fragment from each strain was excised from an agarose gel and directly sequenced, using as sequencing primers in the dideoxy method (Sanger et al., 1977) the same oligonucleotides that were used for PCR amplification.

The results of the sequence analysis reveal that one or both of two point mutations in the promoter region are responsible for the large difference in CGTase production observed.

Strains SJ1599 and 1603–06, all low-yielding, have the promoter sequence shown in SEQ ID NO: 4. However, the high-yielding strain SJ1608 contains the promoter sequence shown in SEQ ID NO: 6.

The differences occur at pos. 553, where SJ1608 contains a C instead of a T, and at pos. 593, where SJ1608 contains a A instead of a T.

The sequence of the amyL promoter present on pSJ1359 and pSJ1391 was determined using the PCR amplification and sequencing procedure described above. This showed that both plasmids contain the promoter sequence shown in SEQ ID NO: 1, i.e. identical to the promoter sequence of SJ1608.

6. Analysis of the promoter effect on expression of the *B. licheniformis* α-amylase gene amyL pSJ1755 (FIG. 28) was constructed by ligating the 3.3 kb BglII-HindIII fragment from pDN1981 (cf. Example 2) to the 4.9 kb BglII-HindIII fragment from pSJ1391 (FIG. 25), selecting for kanamycin resistance (10 µg/ml) in DN1885 at 30° C. This plasmid contains the entire amyL gene with the promoter sequence shown in SEQ ID NO: 6 (the promoter found in the high-yielding CGTase strain SJ1608) on a vector which is temperature-sensitive for replication and conferring resistance to kanamycin and erythromycin.

The α-amylase-producing B. licheniformis strain from which SJ1608 was derived contained a chloramphenicol resistance gene inserted into the alkaline protease gene, thereby disrupting this gene and making the strain alkaline protease negative. A derivative strain, SJ1707, is identical to SJ1608 except that the chloramphenicol resistance gene was replaced by an approximately 150 bp deletion which also makes the strain alkaline protease negative.

Plasmid pSJ1755 was introduced into strain SJ1707 by protoplast transformation, and replacement of the amyL-cgtA fusion gene by the amyL gene was achieved by integration/excision as described in Example 4.

Yields of α-amylase from the transformed strain SJ1707 in which the amyL gene is preceded by the promoter sequence shown in SEQ ID NO: 6 were compared to the yield from the strain from which SJ1608 was derived and in which the amyL gene is preceded by the promoter sequence shown in SEQ ID NO: 4.

The results obtained from BPX shake flask cultures incubated for 6 days at 37° C.

| Promoter sequence | amylase, arbitrary units |
|---|---|
| SEQ ID NO: 4 | 1 |
| SEQ ID NO: 6 | 105 |

It clearly appears from these results that the yield of α-amylase is greatly increased using the promoter sequence shown in SEQ ID#6.

REFERENCES

Akamatzu, T., Sekiguchi, J. (1984). An improved method of protoplast regeneration for Bacillus species and its application to protoplast fusion and transformation. Agric. Biol. Chem., 48, 651–655.

Diderichsen, B., Christiansen, L. (1988). Cloning of a maltogenic alpha-amylase from a Bacillus stearothermophilus. FEMS Microbiology Letters, 56, 53–60.

Jorgensen, P. L., Hansen, C. K., Poulsen, G. B., Diderichsen, B. (1990). In vivo genetic engineering: homologous recombination as a tool for plasmid construction. Gene 96, 37–41.

Diderichsen, B. In: Bacillus Molecular Genetics and Biotechnology Applications, A. T. Ganesan and J. A. Hoch, eds., Academic Press, 1986, pp. 35–46.

Diderichsen, B., Wedsted, U., Hedegaard, L., Jensen, B. R., Sjoholm, C. (1990). Cloning of aldB, which encodes α-acetolactate decarboxylase, an exoenzyme from Bacillus brevis. Journal of Bacteriology, 172, 4315–4321.

Jorgensen, P. L., Poulsen, G. B., Diderichsen, B. (1991). Cloning of a chromosomal α-amylase gene from Bacillus stearothermophilus. FEMS Microbiology Letters, 77, 271–276.

Jorgensen, S., Skov, K. W., Diderichsen, B. (1991). Cloning, sequence, and expression of a lipase gene from Pseudomonas cepacia: Lipase production in heterologous hosts requires two Pseudomonas genes. Journal of Bacteriology, 173, 559–567.

Horinouchi, S., Weisblum, B. (1982a). Nucleotide sequence and functional map of pC194, a plasmid that specifies chloramphenicol resistance. J. Bacteriol., 150, 815–825.

Horinouchi, S., Weisblum, B. (1982b). Nucleotide sequence and functional map of pE194, a plasmid that specifies inducible resistance to macrolide, lincosamide, and streptogramin type B antibiotics. J. Bacteriol. 150, 804–814.

Kieser, T. (1984). Factors affecting the isolation of CCC DNA from Streptomyces lividans and Escherichia coli. Plasmid 12, 19–36.

Mandel, A., Higa, A. (1970). J. Mol. Biol. 53, 159–162.

Mottes, M., Grandi, G., Sgaramella, V., Canosi, U., Morelli, G., Trautner, T. A. (1979). Different specific activities af monomeric and oligomeric forms of plasmid DNA in transformation of Bacillus subtilis and Escherichia coli. Mol. Gen. Genet., 174, 281–286.

Lacey, R., Chopra, L (1974). Genetic studies of a multiresistant strain of Staphylococcus aureus. J. Med. Microbiol., 7, 285–297.

McKenzie, T., Hoshino, T., Tanaka, T., Sueoka, N. (1986). The nucleotide sequence of pUB110: Some salient features in relation to replication and its regulation. Plasmid 15, 93–103.

Sanger, F., Nicklen, S., Coulson, A. R. (1977). DNA sequencing with chain-terminating inhibitors. Proc. Natl. Acad. Sci. USA, 74, 5463–5467.

Saiki, R. K., Gelfand, D. H., Stoffel, S., Scharf, S. J., Higuchi, R., Horn, G. T., Mullis, K. B., Erlich, H. A. (1988). Primer-directed enzymatic amplification of DNA with a thermostable DNA polymerase. Science 239, 487–491.

Gryczan, T., Contente, S., Dubnau, D. (1978). Characterization of Staphylococcus aureus plasmids introduced by transformation into Bacillus subtilis. J. Bacteriol., 134, 318–329.

Yanish-Perron, C., Vieira, J., Messing, J. (1985). Improved M13 phage cloning vectors and host strains: nucleotide sequences of the M13 mp18 and pUC19 vectors. Gene 33, 103–119.

Yasbin, R. E., Williams, G. A., Young, F. E. (1975). J. Bacteriol. 121, 296–304.

We claim:
1. A Bacillus promoter comprising:

GCATGCGTCC TTCTTTGTGC TTGGAAGCAG AGCCCAATAT

TATCCCGAAA CGATAAAACG GATGCTGAAG GAAGGAAACG

AAGTCGGCAA CCATTCCTGG GACCCATCCG TTATTGACAA

GGCTGTCAAA CGAAAAAGCG TATCAGGAGA TTAACGACAC

GCAAGAAATG ATCGAAAAAA TCAGCGGACA CCTGCCTGTA

CACTTGCGTC CTCCATACGG CGGGATCAAT GATTCCGTCC

GCTCGCTTTC CAATCTGAAG GTTTCATTGT GGGATGTTGA

TCCGGAAGAT TGGAAGTACA AAAATAAGCA AAAGATTGTC

AATCATGTCA TGAGCCATGC GGGAGACGGA AAAATCGTCT

TAATGCACGA TATTTATGCA ACGTTCGCAG ATGCTGCTGA

AGAGATTATT AAAAAGCTGA AAGCAAAAGG CTATCAATTG

GTAACTGTAT CTCAGCTTGA AGAAGTGAAG AAGCAGAGAG

GCTATTGAAT AAATGAGTAG AAAGCGCCAT ATCGGCGCTT

TTCTTTTGGA AGAAAATATA GGGAAAATGG TAN$^1$TTGTTAA

AAATTCGGAA TATTTATACA ATATCATN$^2$N$^3$N$^4$

N$^5$N$^6$N$^7$N$^8$N$^9$CATTG AAAGGGGAGG AGAATC (SEQ ID NO: 1), or fragments of SEQ ID NO: 1 comprising N$^2$–N$^9$ and having promoter activity, wherein N$^1$ is C, N$^3$–N$^9$ is A, T, C or G, and N$^2$ is A or G provided that N$^2$–N$^9$ do not together form the sequence ATGTTTCA or GTGTTTCA.

2. The promoter according to claim 1, wherein N$^7$ is A, G or C.

3. The promoter according to claim 1, wherein N$^7$ is A.

4. The promoter according to claim 1, wherein N$^2$–N$^9$ together form the sequence ATGTTACA.

5. A DNA construct comprising a DNA sequence coding for a protein preceded by a promoter according to claim 1.

6. The DNA construct according to claim 5, wherein the protein is an enzyme.

7. The DNA construct according to claim 6, wherein the enzyme is an α-amylase, cyclodextrin glycosyl transferase or protease.

8. The DNA construct according to claim 5, which further comprises a DNA sequence coding for a signal peptide upstream of the DNA sequence coding for the protein.

9. The DNA construct according to claim 8, wherein the signal peptide is the *B. licheniformis* α-amylase signal peptide.

10. A recombinant expression vector comprising a DNA construct according to claim 5.

11. A Bacillus host cell transformed with a DNA construct according to claim 5.

12. A host cell according to claim 11, wherein the strain is a strain of *Bacillus licheniformis, Bacillus lentus, Bacillus brevis, Bacillus stearothermophilus, Bacillus alkalophilus, Bacillus amyloliquefaciens, Bacillus coagulans, Bacillus thuringiensis* or *Bacillus subtilis*.

13. A process for producing a protein, comprising
 (a) culturing a host cell according to claim 11 under conditions permitting production of the protein; and
 (b) recovering the protein from the culture.

14. A Bacillus host cell transformed with an expression vector according to claim 10.

15. The host cell according to claim 14, wherein the strain is a strain of *Bacillus licheniformis, Bacillus lentus, Bacillus brevis, Bacillus stearothermophilus, Bacillus alkalophilus, Bacillus amyloliquefaciens, Bacillus coagulans, Bacillus thuringiensis* or *Bacillus subtilis*.

16. A process for producing a protein, comprising
 (a) culturing a host cell according to claim 14 under conditions permitting production of the protein; and
 (b) recovering the protein from the culture.

17. A Bacillus promoter comprising:

DTATCAATTG GTAACTGTAT CTCAGCTTGA
AGAAGTGAAG AAGCAGAGAG GCTATTGAAT
AAATGAGTAG AAAGCGCCAT ATCGGCGCTT
TTCTTTTGGA AGAAAATATA GGGAAAATGG
TAN$^1$TTGTTAA AAATTCGGAA TATTTATACA
ATATCATN$^2$N$^3$N$^4$ N$^5$N$^6$N$^7$N$^8$N$^9$CATTG AAAGGGGAGG
AGAATC (SEQ ID NO: 2), or fragments of SEQ ID NO:2 comprising N$^2$–N$^9$ and having promoter activity, wherein N$^1$ is C, N$^3$–N$^9$ is A, T, C or G, and N$^2$ is A or G provided that N$^2$–N$^9$ do not together form the sequence ATGTTTCA or GTGTTTCA.

18. The promoter according to claim 17, wherein N$^7$ is A, G or C.

19. The promoter according to claim 17, wherein N$^7$ is A.

20. The promoter according to claim 17, wherein N$^2$–N$^9$ together form the sequence ATGTTACA.

21. A DNA construct comprising a DNA sequence coding for a protein preceded by a promoter according to claim 17.

22. The DNA construct according to claim 21, wherein the protein is an enzyme.

23. The DNA construct according to claim 22, wherein the enzyme is an α-amylase, cyclodextrin glycosyl transferase or protease.

24. The DNA construct according to claim 21, which further comprises a DNA sequence coding for a signal peptide upstream of the DNA sequence coding for the protein.

25. The DNA construct according to claim 24, wherein the signal peptide is the *B. licheniformis* α-amylase signal peptide.

26. A recombinant expression vector comprising a DNA construct according to claim 21.

27. A Bacillus host cell transformed with a DNA construct according to claim 21.

28. A host cell according to claim 27, wherein the strain is a strain of *Bacillus licheniformis, Bacillus lentus, Bacillus brevis, Bacillus stearothermophilus, Bacillus alkalophilus, Bacillus amyloliquefaciens, Bacillus coagulans, Bacillus thuringiensis* or *Bacillus subtilis*.

29. A process for producing a protein, comprising
 (a) culturing a host cell according to claim 28 under conditions permitting production of the protein; and
 (b) recovering the protein from the culture.

30. A Bacillus host cell transformed with an expression vector according to claim 26.

31. The host cell according to claim 30, wherein the strain is a strain of *Bacillus licheniformis, Bacillus lentus, Bacillus brevis, Bacillus stearothermophilus, Bacillus alkalophilus, Bacillus amyloliquefaciens, Bacillus coagulans, Bacillus thuringiensis* or *Bacillus subtilis*.

32. A process for producing a protein, comprising
 (a) culturing a host cell according to claim 30 under conditions permitting production of the protein; and
 (b) recovering the protein from the culture.

* * * * *

UNITED STATES PATENT AND TRADEMARK OFFICE
CERTIFICATE OF CORRECTION

PATENT NO.     :     5,698,415

DATED          :     December 16, 1997

INVENTOR(S)    :     Jørgensen et al.

It is certified that error appears in the above-identified patent and that said Letters Patent is hereby corrected as shown below:

On the Front Cover of the Patent, left column, after Assignee: delete "Novo Nordisk Als" and insert --Novo Nordisk A/S--.

Signed and Sealed this

Seventeenth Day of March, 1998

*Attest:*

BRUCE LEHMAN

*Attesting Officer*          Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:

(A) LENGTH: 607 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:1:

```
GCATGCGTCC TTCTTTGTGC TTGGAAGCAG AGCCCAATAT TATCCCGAAA CGATAAAACG      60
GATGCTGAAG GAAGGAAACG AAGTCGGCAA CCATTCCTGG GACCCATCCG TTATTGACAA     120
GGCTGTCAAA CGAAAAGCG  TATCAGGAGA TTAACGACAC GCAAGAAATG ATCGAAAAAA     180
TCAGCGGACA CCTGCCTGTA CACTTGCGTC CTCCATACGG CGGATCAAT  GATTCCGTCC     240
GCTCGCTTTC CAATCTGAAG GTTTCATTGT GGATGTTGA  TCCGGAAGAT TGGAAGTACA     300
AAAATAAGCA AAAGATTGTC AATCATGTCA TGAGCCATGC GGGAGACGGA AAAATCGTCT     360
TAATGCACGA TATTTATGCA ACGTTCGCAG ATGCTGCTGA AGAGATTATT AAAAAGCTGA     420
AAGCAAAAGG CTATCAATTG GTAACTGTAT CTCAGCTTGA AGAAGTGAAG AAGCAGAGAG     480
GCTATTGAAT AAATGAGTAG AAAGCGCCAT ATCGGCGCTT TTCTTTTGGA AGAAAATATA     540
GGGAAAATGG TATTGTTAAA AATTCGGAAT ATTTATACAA TATCATCATT GAAAGGGGAG     600
GAGAATC                                                              607
```

(2) INFORMATION FOR SEQ ID NO: 2:

(i) SEQUENCE CHARACTERISTICS:
(A) LENGTH: 186 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO: 2:

```
CTATCAATTG GTAACTGTAT CTCAGCTTGA AGAAGTGAAG AAGCAGAGAG GCTATTGAAT      60
AAATGAGTAG AAAGCGCCAT ATCGGCGCTT TTCTTTTGGA AGAAAATATA GGGAAAATGG     120
TANTTGTTAA AAATTCGGAA TATTTATACA ATATCATNNN NNNNNCATTG AAAGGGGAGG     180
AGAATC                                                               186
```

(2) INFORMATION FOR SEQ ID NO: 3:

(i) SEQUENCE CHARACTERISTICS:
(A) LENGTH: 66 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO: 3:

```
TCGACTGATC ACTTGCTGCC TCATTCTGCA GCAGCGGCGG CACCGGATAC TTCAGTTTCT      60
CTAGAG                                                                66
```

(2) INFORMATION FOR SEQ ID NO: 4:

(i) SEQUENCE CHARACTERISTICS:
(A) LENGTH: 616 base pairs
(B) TYPE: nucleic acid
(C) STRANDEDNESS: single
(D) TOPOLOGY: linear (i i) MOLECULE TYPE: DNA (genomic)

( x i ) SEQUENCE DESCRIPTION: SEQ ID NO: 4:

```
GCATGCGTCC   TTCTTTGTGC   TTGGAAGCAG   AGCCCAATAT   TATCCCGAAA   CGATAAAACG    60
GATGCTGAAG   GAAGGAAACG   AAGTCGGCAA   CCATTCCTGG   GACCCATCCG   TTATTGACAA   120
GGCTGTCAAA   CGAAAAGCG    TATCAGGAGA   TTAACGACAC   GCAAGAAATG   ATCGAAAAA    180
TCAGCGGACA   CCTGCCTGTA   CACTTGCGTC   CTCCATACGG   CGGGATCAAT   GATTCCGTCC   240
GCTCGCTTTC   CAATCTGAAG   GTTCATTGT    GGGATGTTGA   TCCGGAAGAT   TGGAAGTACA   300
AAAATAAGCA   AAAGATTGTC   AATCATGTCA   TGAGCCATGC   GGGAGACGGA   AAAATCGTCT   360
TAATGCACGA   TATTTATGCA   ACGTTCGCAG   ATGCTGCTGA   AGAGATTATT   AAAAAGCTGA   420
AAGCAAAAGG   CTATCAATTG   GTAACTGTAT   CTCAGCTTGA   AGAAGTGAAG   AAGCAGAGAG   480
GCTATTGAAT   AAATGAGTAG   AAAGCGCCAT   ATCGGCGCTT   TCTTTTGGA    AGAAAATATA   540
GGGAAAATGG   TATTTGTTAA   AAATTCGGAA   TATTTATACA   ATATCATATG   TTTCACATTG   600
AAAGGGGAGG   AGAATC                                                          616
```

( 2 ) INFORMATION FOR SEQ ID NO: 5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 5:

```
CCTGTTGGAT   TATTACTGGG                                                       20
```

( 2 ) INFORMATION FOR SEQ ID NO: 6:

( i ) SEQUENCE CHARACTERISTICS:
        ( A ) LENGTH: 616 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 6:

```
GCATGCGTCC   TTCTTTGTGC   TTGGAAGCAG   AGCCCAATAT   TATCCCGAAA   CGATAAAACG    60
GATGCTGAAG   GAAGGAAACG   AAGTCGGCAA   CCATTCCTGG   GACCCATCCG   TTATTGACAA   120
GGCTGTCAAA   CGAAAAGCG    TATCAGGAGA   TTAACGACAC   GCAAGAAATG   ATCGAAAAAA   180
TCAGCGGACA   CCTGCCTGTA   CACTTGCGTC   CTCCATACGG   CGGGATCAAT   GATTCCGTCC   240
GCTCGCTTTC   CAATCTGAAG   GTTCATTGT    GGGATGTTGA   TCCGGAAGAT   TGGAAGTACA   300
AAAATAAGCA   AAAGATTGTC   AATCATGTCA   TGAGCCATGC   GGGAGACGGA   AAAATCGTCT   360
TAATGCACGA   TATTTATGCA   ACGTTCGCAG   ATGCTGCTGA   AGAGATTATT   AAAAAGCTGA   420
AAGCAAAAGG   CTATCAATTG   GTAACTGTAT   CTCAGCTTGA   AGAAGTGAAG   AAGCAGAGAG   480
GCTATTGAAT   AAATGAGTAG   AAAGCGCCAT   ATCGGCGCTT   TCTTTTGGA    AGAAAATATA   540
GGGAAAATGG   TACTTGTTAA   AAATTCGGAA   TATTTATACA   ATATCATATG   TTACACATTG   600
AAAGGGGAGG   AGAATC                                                          616
```